United States Patent
Wang et al.

(10) Patent No.: US 11,426,706 B2
(45) Date of Patent: Aug. 30, 2022

(54) CATION EXCHANGE CHROMATOGRAPHY WASH BUFFER

(71) Applicant: Cephalon, Inc., Frazer, PA (US)

(72) Inventors: Lu Wang, West Chester, PA (US); Albert Kao, West Chester, PA (US); Zhaoqing Zhang, West Chester, PA (US); Mi Jin, West Chester, PA (US); Tianyi Zhou, West Chester, PA (US)

(73) Assignee: Cephalon, Inc., Frazer, PA (US)

( * ) Notice: Subject to any disclaimer, the term of this patent is extended or adjusted under 35 U.S.C. 154(b) by 741 days.

(21) Appl. No.: 16/014,778

(22) Filed: Jun. 21, 2018

(65) Prior Publication Data
US 2019/0046956 A1    Feb. 14, 2019

Related U.S. Application Data

(60) Provisional application No. 62/523,038, filed on Jun. 21, 2017.

(51) Int. Cl.
*B01D 15/36* (2006.01)
*C07K 1/18* (2006.01)
(Continued)

(52) U.S. Cl.
CPC .......... *B01J 20/286* (2013.01); *B01D 15/362* (2013.01); *B01J 20/28026* (2013.01); *C07K 1/18* (2013.01); *C07K 1/22* (2013.01); *C07K 16/00* (2013.01); *C07K 16/18* (2013.01); *C07K 16/2875* (2013.01); *C07K 16/2896* (2013.01); *C12Q 1/686* (2013.01); *C07K 2317/565* (2013.01)

(58) Field of Classification Search
None
See application file for complete search history.

(56) References Cited

U.S. PATENT DOCUMENTS

| | | |
|---|---|---|
| 2003/0153735 A1 | 8/2003 | Breece et al. |
| 2009/0148435 A1 | 6/2009 | Lebreton et al. |
| | (Continued) | |

FOREIGN PATENT DOCUMENTS

| | | |
|---|---|---|
| EP | 2703007 A1 | 3/2014 |
| WO | WO-2007054809 A2 | 5/2007 |
| | (Continued) | |

OTHER PUBLICATIONS

SP Sepharose Fast Flow.*
(Continued)

*Primary Examiner* — Kara M Peo
(74) *Attorney, Agent, or Firm* — Sterne, Kessler, Goldstein & Fox P.L.L.C.

(57) ABSTRACT

A wash buffer comprising a surfactant for use in affinity and cation exchange chromatography to purify proteins of interest from protein aggregates and to remove and/or inactivate viruses. When used during affinity or cation exchange chromatography for the purification of a protein of interest, such as an antibody, the wash buffer significantly improves viral clearance from the preparation, while also reducing the levels of host cell proteins and protein aggregates. Following affinity or cation exchange chromatography with the wash buffer, the protein of interest may be further purified using other chromatography and filtration operations.

28 Claims, 1 Drawing Sheet

Specification includes a Sequence Listing.

(51) Int. Cl.
*B01J 20/286* (2006.01)
*B01J 20/28* (2006.01)
*C07K 1/22* (2006.01)
*C07K 16/18* (2006.01)
*C12Q 1/686* (2018.01)
*C07K 16/00* (2006.01)
*C07K 16/28* (2006.01)

(56) References Cited

U.S. PATENT DOCUMENTS

| | | | |
|---|---|---|---|
| 2009/0220489 A1 | 9/2009 | Zeller et al. | |
| 2011/0305711 A1 | 12/2011 | Allan et al. | |
| 2014/0238935 A1* | 8/2014 | Komkova | B01J 20/3285 210/635 |
| 2014/0255302 A1 | 9/2014 | Poulton et al. | |
| 2015/0313965 A1 | 11/2015 | Pogue et al. | |
| 2016/0068612 A1 | 3/2016 | Clarke et al. | |
| 2016/0108127 A1* | 4/2016 | Brower | C07K 16/2839 530/387.1 |
| 2018/0021696 A1 | 1/2018 | Wang | |

FOREIGN PATENT DOCUMENTS

| | | |
|---|---|---|
| WO | WO-2011037983 A1 | 3/2011 |
| WO | WO-2012064682 A1 | 5/2012 |
| WO | WO-2015073580 A1 | 5/2015 |
| WO | WO-2016146680 A1 | 9/2016 |
| WO | WO-2018022628 A1 | 2/2018 |

OTHER PUBLICATIONS

Connell-Crowley, L., et al. "Cation exchange chromatography provides effective retrovirus clearance for antibody purification processes," *Biotechnol. Bioeng.* 109:157-165, John Wiley & Sons, United States (2012).

GE Healthcare Life Sciences, "Process-scale Purification of Monoclonal Antibodies—Polishing using Capto™ Q," accessed at https://www.gelifesclences.com/gehcls_images/GELS/Related%20Content/Files/13147509l3712/litdoc28903716_20161014161829.pdf on 2006.

Holstein et al., Protein A Intermediate Wash Strategies, BioProcess International, Feb. 6, 2015, [retrieved on Sep. 29, 2017, Accessed at [http://www.bioprocessintl.com/downstreamprocessing/chromatography/protein-intermediate-wash-strategies/] p. 1, para 1, p. 6.

Liu, H.F., et al., "Recovery and Purification Process Development for Monoclonal Antibody Production," mAbs 2(5):480-499, Taylor & Francis, United States (2010).

Miesegaes, G., et al., "Analysis of viral clearance unit operations for monoclonal antibodies," Biotechnol. Bioeng. 106:238-246, John Wiley & Sons, United States (2010).

Miesegaes, G., et al., "Monoclonal antibody capture and viral clearance by cation exchange chromatography," Biotechnol. Bioeng. 109:2048-2058, John Wiley & Sons, United States (2012).

Roguska, M.A., et al., "A Comparison of Two Murine Monoclonal Antibodies Humanized by CDR-grafting and Variable Domain Resurfacing," Protein Engineering 9(10):895-904, Oxford University Press, England (1996).

Shukla, A.A., et al., "Downstream Processing of Monoclonal Antibodies—Application of Platform Approaches," Journal of chromatography B 848(1):28-39, Elsevier, Netherlands (2007).

Thermo Fisher Scientific Inc. Instructions Pierce Protein Refolding Kit (2010) [retrieved on Oct. 14, 2017), Accessed at [https://assets.thermofisher.com/TFS-Assets/LSG/manuals/MAN0011490_Pierce_Protein_Refolding_UG.pdf,] p. 1, Description, Base Refolding Buffer 5, 6 and 8-9.

International Search Report and Written Opinion for International Application No. PCT/US2017/43743, International Search Authority, United States, dated Sep. 12, 2016, 16 pages.

International Search Report and Written Opinion for International Application No. PCT/US2018/038777, ISA/US, Alexandria, Virginia, daed Nov. 5, 2018, 13 pages.

* cited by examiner

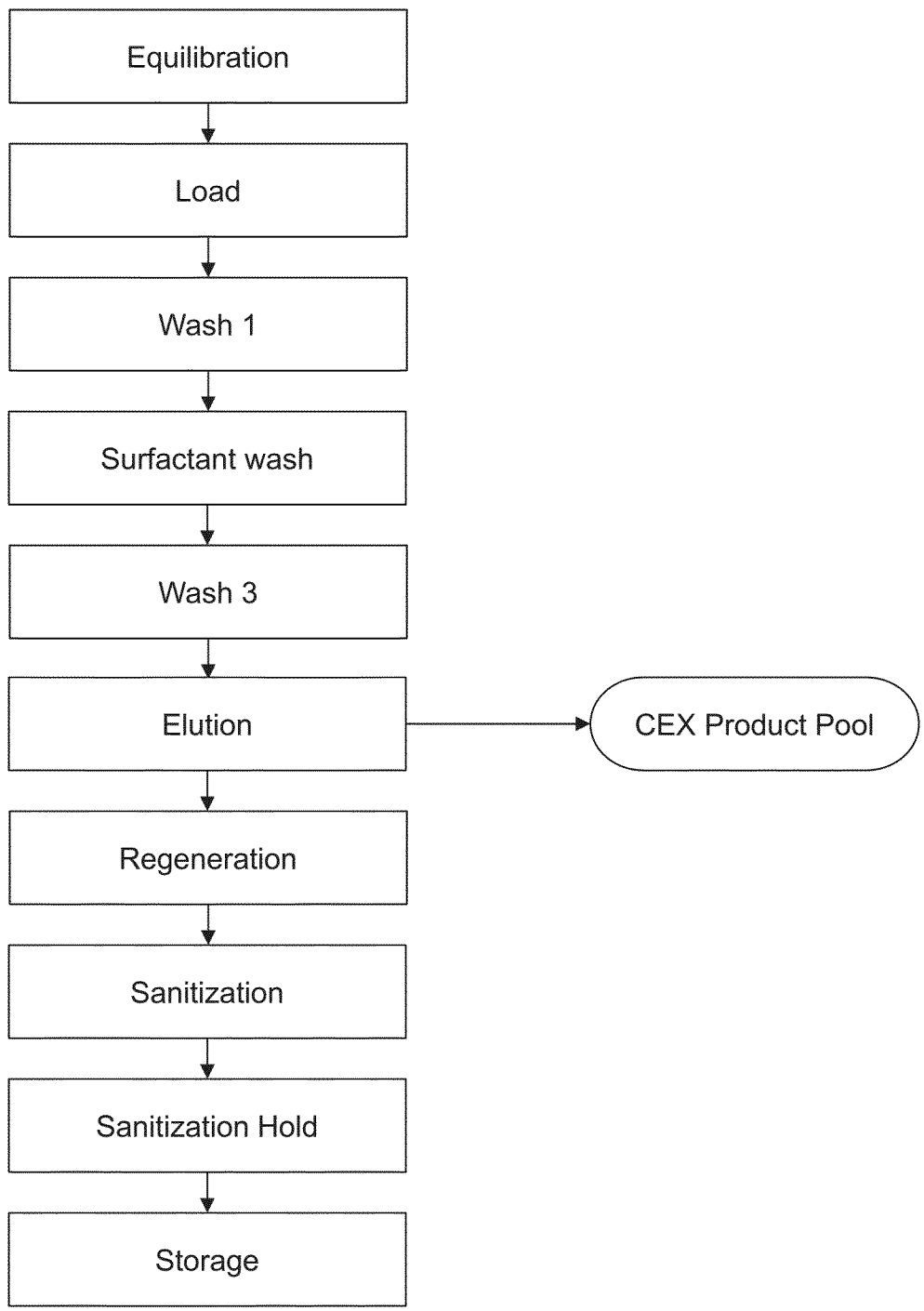

SEQUENCE LISTING

<160> NUMBER OF SEQ ID NOS: 10

<210> SEQ ID NO 1
<211> LENGTH: 122
<212> TYPE: PRT
<213> ORGANISM: Artificial Sequence
<220> FEATURE:
<223> OTHER INFORMATION: Anti-CGRP VH

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
        115                 120
```

<210> SEQ ID NO 2
<211> LENGTH: 107
<212> TYPE: PRT
<213> ORGANISM: Artificial Sequence
<220> FEATURE:
<223> OTHER INFORMATION: Anti-CGRP VL

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys
            100                 105

<210> SEQ ID NO 3
<211> LENGTH: 120
<212> TYPE: PRT
<213> ORGANISM: Artificial Sequence
<220> FEATURE:
<223> OTHER INFORMATION: Anti-CD38 VH

<400> SEQUENCE: 3

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Ser
            20                  25                  30

Val Met Asn Trp Val Gln Gln Ala Pro Gly Lys Gly Leu Glu Trp Met
        35                  40                  45

Gly Trp Ile Asp Pro Glu Tyr Gly Arg Thr Asp Val Ala Glu Lys Phe
50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Lys Tyr Asn Ser Gly Tyr Gly Phe Pro Tyr Trp Gly Gln
            100                 105                 110

Gly Thr Thr Val Thr Val Ser Ser
        115                 120

<210> SEQ ID NO 4
<211> LENGTH: 108
<212> TYPE: PRT
<213> ORGANISM: Artificial Sequence
<220> FEATURE:
<223> OTHER INFORMATION: Anti-CD38 VL

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asp Ser Asp
            20                  25                  30

Val Asp Trp Tyr Gln Gln Lys Pro Gly Lys Ala Pro Lys Leu Leu Ile
        35                  40                  45

Tyr Lys Ala Ser Asn Asp Tyr Thr Gly Val Pro Ser Arg Phe Ser Gly
            50                  55                  60
Ser Gly Ser Gly Thr Asp Phe Thr Phe Thr Ile Ser Ser Leu Gln Pro
 65                  70                  75                  80
Glu Asp Ile Ala Thr Tyr Tyr Cys Met Gln Ser Asn Thr His Pro Arg
                    85                  90                  95
Thr Phe Gly Gly Gly Thr Lys Val Glu Ile Lys Arg
                100                 105

<210> SEQ ID NO 5
<211> LENGTH: 119
<212> TYPE: PRT
<213> ORGANISM: Artificial Sequence
<220> FEATURE:
<223> OTHER INFORMATION: Anti-TL1a VH1

<400> SEQUENCE: 5

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
                20                  25                  30
Asp Ile Asn Trp Val Arg Gln Ala Pro Gly Gln Gly Leu Glu Trp Met
            35                  40                  45
Gly Trp Leu Asn Pro Asn Ser Gly Asn Thr Gly Tyr Ala Gln Lys Phe
    50                  55                  60
Gln Gly Arg Val Thr Met Thr Ala Asp Arg Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Glu Val Pro Glu Thr Ala Ala Phe Gly Tyr Trp Gly Gln Gly
                100                 105                 110
Thr Leu Val Thr Val Ser Ser
            115

<210> SEQ ID NO 6
<211> LENGTH: 119
<212> TYPE: PRT
<213> ORGANISM: Artificial Sequence
<220> FEATURE:
<223> OTHER INFORMATION: Anti-TL1a VH2

<400> SEQUENCE: 6

Gln Val Gln Leu Val Gln Ser Gly Ala Glu Val Lys Lys Pro Gly Ala
 1               5                  10                  15
Ser Val Lys Val Ser Cys Lys Ala Ser Gly Tyr Thr Phe Thr Ser Tyr
                20                  25                  30
Asp Ile Asn Trp Val Arg Gln Ala Pro Gly Gln Gly Leu Glu Trp Met
            35                  40                  45
Gly Trp Leu Asn Pro Asn Ser Gly Tyr Thr Gly Tyr Ala Gln Lys Phe
    50                  55                  60
Gln Gly Arg Val Thr Met Thr Ala Asp Arg Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Arg Glu Val Pro Glu Thr Ala Ala Phe Gly Tyr Trp Gly Gln Gly
                100                 105                 110
Thr Leu Val Thr Val Ser Ser
            115

```
<210> SEQ ID NO 7
<211> LENGTH: 111
<212> TYPE: PRT
<213> ORGANISM: Artificial Sequence
<220> FEATURE:
<223> OTHER INFORMATION: Anti-TL1a VL
<220> FEATURE:
<221> NAME/KEY: MISC_FEATURE
<222> LOCATION: (32)..(32)
<223> OTHER INFORMATION: Xaa 32 is G or A
<220> FEATURE:
<221> NAME/KEY: MISC_FEATURE
<222> LOCATION: (33)..(33)
<223> OTHER INFORMATION: Xaa 33 is L or S or Q
<220> FEATURE:
<221> NAME/KEY: MISC_FEATURE
<222> LOCATION: (36)..(36)
<223> OTHER INFORMATION: Xaa 36 is H or L
<220> FEATURE:
<221> NAME/KEY: MISC_FEATURE
<222> LOCATION: (93)..(93)
<223> OTHER INFORMATION: Xaa 93 is Y or F or W

<400> SEQUENCE: 7

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Xaa
            20                  25                  30

Xaa Gly Val Xaa Trp Tyr Gln Gln Leu Pro Gly Thr Ala Pro Lys Leu
            35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Xaa Asp Gly Thr
                85                  90                  95

Leu Ser Ala Leu Phe Gly Gly Gly Thr Lys Leu Thr Val Leu Gly
            100                 105                 110

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cctgagtcac cggactgcat                                           20

<210> SEQ ID NO 9
<211> LENGTH: 18
<212> TYPE: DNA
<213> ORGANISM: Artificial Sequence
<220> FEATURE:
<223> OTHER INFORMATION: Primer
```

```
<400> SEQUENCE: 9
accagtcgcg agctggag                                                        18

<210> SEQ ID NO 10
<211> LENGTH: 16
<212> TYPE: DNA
<213> ORGANISM: Artificial Sequence
<220> FEATURE:
<223> OTHER INFORMATION: Primer

<400> SEQUENCE: 10
agggagctac aggcgg                                                          16
```

CATION EXCHANGE CHROMATOGRAPHY WASH BUFFER

CROSS REFERENCE TO RELATED APPLICATIONS

This application relates to U.S. Provisional Application No. 62/523,038 filed on Jun. 21, 2017, the content of which is incorporated by reference herein, in its entirety and for all purposes.

REFERENCE TO A SEQUENCE LISTING SUBMITTED ELECTRONICALLY VIA EFSWEB

The content of the electronically submitted sequence listing (Name: 2873_2770001_ST25; Size: 8,802 bytes; and Date of Creation: Jun. 20, 2018) is herein incorporated by reference in its entirety.

BACKGROUND OF THE INVENTION

Field of the Invention

The invention relates generally to the field of protein biochemistry. More particularly, the invention relates to wash buffers used in cation exchange chromatography to purify target proteins, e.g., antibodies, from protein aggregates and to remove and/or inactivate viruses. Washing a cation exchange chromatography support with a buffer containing one or more surfactants has been found to substantially improve viral clearance from the protein preparation.

Background Art

Recombinant proteins are expressed in host cells and typically purified by a series of chromatography and filtration steps. Traditionally, a monoclonal antibody (mAb) purification process flow is composed of three chromatography columns. The major function of each chromatography column is listed below:
  Protein A (ProA) for product recovery and host cell protein (HCP) removal;
  Cation exchange (CEX) for DNA, HCP and aggregate removal; and
  Anion exchange (AEX) for further DNA and HCP removal, and viral clearance.
A typical purification scheme, also known as a downstream cascade, employs affinity chromatography followed by cation exchange chromatography (CEX) or hydrophobic interaction chromatography (HIC) followed by anion exchange chromatography (AEX). CEX chromatography and AEX are usually considered as polishing steps (See, e.g., GE Healthcare. (2006). Process-scale purification of monoclonal antibodies—polishing using Capto™ Q. www.gelifesciences.com/gehcls_images/GELS/Related %20Content/Files/1314750913712/litdoc28903716_20130507212449.PDF). Additionally, a typical downstream purification scheme also includes a viral inactivation step and viral filtration step to ensure adequate viral clearance.

Unfortunately, each additional chromatographic step typically reduces the overall protein yield. Moreover, the use of additional chromatography steps increases the expense and operating complexity of the process.

Reducing or eliminating polishing chromatographic steps by improving the performance of the cation exchange chromatography step can significantly reduce the development efforts and manufacturing cost, improve target product recovery, as well as simplify manufacturing operations. However, one of the major concerns of using CEX as the only polishing step is that it is not considered as a robust viral clearance step (as shown in metadata analysis from multiple studies; Miesegaes et al. Biotechnol. Bioeng. 2010; 106:238-246).

For a CEX step to achieve adequate process performance, and in particular, effective viral clearance, the operating design space in terms of process parameters is significantly limited (Miesegaes, G. R. et al. Biotechnol. Bioeng. 2012; 109:2048-2058 2 and Connell-Crowley, L. et al. Biotechnol. Bioeng. 2012; 109: 157-165.)

The present invention provides a wash procedure applied in a cation exchange step to improve the chromatography performance, in particular the viral clearance capability of this step. The application of the wash procedure, and its associated robust viral clearance capability, can enable the removal of certain other polishing chromatography steps, such as AEX, resulting in reduced number of chromatography steps needed.

The application of the wash procedure described herein can also enable the removal of a viral inactivation step, which is especially useful for molecules not stable under typical viral inactivation conditions (e.g. low pH), or in a process where viral inactivation may be challenging to implement (e.g. continuous processing), and still achieve adequate viral clearance from downstream unit operations from chromatography and filtration steps.

SUMMARY OF THE INVENTION

It has been found that by increasing viral clearance capability on a CEX support, the AEX chromatography step can be removed to simplify the overall protein, e.g., antibody, manufacturing process. Adding a surfactant to the wash buffer in CEX increases the viral clearance efficiency without compromise impurity clearance capability. This improvement in viral clearance capability of a CEX column is observed irrespective of whether CEX is utilized as a polishing step (i.e. after primary product recovery or capture step on e.g., ProA), or as a primary recovery step, per se.

The wash solutions may be used in a protein purification method, such as a multi-step protein purification method as described above. In another aspect, the disclosure features methods for purifying a protein of interest, which is expressed from a cell, including by recombinant expression or by hybridoma expression. In general, the method comprises loading a mixture of a protein of interest and one or more contaminating viruses onto an CEX chromatography support, washing the support with an aqueous wash solution comprising a surfactant, and then eluting the protein of interest from the support, thereby forming a purified eluate of the protein of interest, wherein the purified eluate does not comprise the contaminating viruses (or comprises a reduced number thereof in comparison to the mixture loaded onto the CEX chromatography support). Optionally the method comprises the step of, after the surfactant wash step and prior to the elution step, washing the support with an intermediate wash buffer comprising no surfactant. The intermediate wash buffer removes any residual surfactant from the preceding wash from the support, prior to the step of elution.

The mixture of the protein of interest may be the eluate of a prior chromatography step, such as the eluate of an affinity chromatography column, optionally a protein A chromatography column. In another embodiment, the mixture of the protein of interest is harvest cell culture fluid (HCCF). In this embodiment, the protein purification method may not comprise an affinity chromatography step (i.e. the CEX chromatography step described herein may replace an affinity chromatography, e.g. protein A step). The aqueous wash solution may be any such solution described or exemplified herein, including those wash solutions described in the following sections. The intermediate wash buffer may be any aqueous CEX wash buffer, such as a CEX equilibration buffer, or any of the CEX wash solutions described herein, with the proviso that it does not contain a surfactant. In one embodiment, the intermediate wash buffer is of the same composition as any one of the CEX wash solutions described herein, without the surfactant.

The method may further comprise acidifying (e.g., lowering the pH of) the purified eluate containing the protein of interest to inactive any remaining viruses in the eluate. Lowering the pH is done for a period of time sufficient to inactivate viruses in the eluate, and then the pH is raised to a more neutral pH. The method may further comprise filtering the purified eluate of the protein of interest to remove viruses, including inactivated viruses. The method may further comprise treating the purified eluate of the protein of interest with diafiltration, ultrafiltration, or both diafiltration and ultrafiltration. The method may further comprise formulating the purified eluate of the protein of interest as a composition including a pharmaceutically acceptable excipient. The method may further comprise formulating the further-purified eluate of the protein of interest as a composition including a pharmaceutically acceptable excipient. In some aspects, the protein purification method does not comprise an anion exchange (column or membrane) chromatography step. In some aspects, the protein purification method does not comprise another polishing chromatography step. In some aspects, the protein purification method does not comprise a viral inactivation step.

In some aspects, a method of purifying a protein of interest bound to a cation exchange (CEX) chromatography support comprises applying a wash solution comprising one or more surfactants to the CEX chromatography support. In some aspects, the method further comprises eluting the protein of interest from the support to form a purified eluate comprising the protein of interest.

In some aspects, a method for purifying a protein of interest comprises loading a mixture comprising a protein of interest and one or more contaminant proteins, aggregates, and/or viruses onto a CEX chromatography support, washing the support with a wash solution comprising one or more surfactants, and then eluting the protein of interest from the support, thereby forming a purified eluate of the protein of interest.

In some aspects, a method for purifying a protein of interest comprises loading a mixture comprising a protein of interest and one or more contaminant proteins, aggregates, and/or viruses onto a CEX chromatography support, washing the support with an aqueous wash solution comprising one or more surfactants to elute the one or more contaminant proteins, aggregates, and/or viruses from the support, and then eluting the protein of interest from the support, thereby forming a purified eluate of the protein of interest.

In some aspects, the one or more surfactants comprises Triton 100, nonyl phenoxypolyethoxylethanol (NP40), Sulfobetaine-12 (SB-12), Sulfobetaine-14 (SB-14), Lauryldimethylamine N-oxide (LDAO), polysorbate 20 (PS 20), polysorbate 80 (PS 80), or a combination thereof. In some aspects, the one or more surfactants comprise a zwitterionic surfactant. In some aspects, the zwitterionic surfactant is 3-[(3-cholamidopropyl)dimethylammonio]-1-propane- sulfonate (CHAPS), or cocamidopropyl hydroxysultaine (CAHS), or a combination thereof. In some aspects, the one or more surfactants comprise a quaternary ammonium salt. In some aspects, the quaternary ammonium salt is cetrimonium bromide (CTAB) or dioctadecyldimethylammonium bromide (DODAB). In some aspects, the one or more surfactants comprise an alkylphenol ethoxylate. In some aspects, the alkylphenol ethoxylate is a nonoxynol, optionally nonaethylene glycol. In some aspects, the one or more surfactants comprise an ethoxylate. In some aspects, the one or more surfactants comprise an alkyl polyglucoside, optionally decyl glucoside. In some aspects, the one or more surfactants comprise an amino oxide. In some aspects, the one or more surfactants comprise a phosphine oxide. In some aspects, the one or more surfactants comprise a non-ionic surfactant. In some aspects, the one or more surfactants comprise an anionic surfactant, optionally wherein the anionic surfactant is sodium dodecyl sulfate (SDS).

In some aspects, the wash solution comprises about 0.01% to about 1% w/v of the one or more surfactants. In some aspects, the wash solution comprises about 0.05% to about 0.5% w/v of the one or more surfactants. In some aspects, the wash solution comprises about 0.1% w/v of the one or more surfactants. In some aspects, the wash solution comprises about 0.2% w/v of the one or more surfactants. In some aspects, the wash solution comprises about 0.5% w/v of the one or more surfactants.

In some aspects, the CEX chromatography support is a sepharose matrix resin. In some aspects, the CEX chromatography support is a synthetic polymer matrix resin. In some aspects, the CEX chromatography support is not a hydrophic resin. In some aspects, the CEX chromatography support is selected from the group consisting of Capto S, Fractogel EMD SO3-, Fractogel EMD TMAE, Fractogel EMD, Eshnumo S. Eshmuno HCX, Tosoh Toyopearl CM, Tosoh Toyopearl SP, and Nuvia cPrime.

In some aspects, the method further comprises applying a subsequent wash solution to the CEX chromatography support before eluting the protein of interest from the support. In some aspects, the subsequent wash solution does not contain a surfactant. In some aspects, the subsequent wash solution removes the surfactant from the support. In some aspects, applying the subsequent wash solution increases host cell protein (HCP) removal as compared to not applying the subsequent solution.

In some aspects, the method further comprises loading a harvest cell culture fluid (HCCF) onto the support prior to applying the wash solution comprising the one or more surfactants to the support. In some aspects, the mixture comprising a protein of interest and one or more contaminant proteins, aggregates, and/or viruses is a HCCF.

In some aspects, the method does not comprise protein A purification.

In some aspects, the method further comprises loading the eluate of a chromatography step onto the support prior to applying the wash solution comprising the one or more surfactants to the support. In some aspects, the mixture comprising a protein of interest and one or more contaminant proteins, aggregates, and/or viruses is an eluate of a chromatography step. In some aspects, the eluate of the chromatography step is an eluate of an affinity chromatography step. In some aspects, the affinity chromatography step is a protein A purification. In some aspects, the protein A purification comprises washing a protein A support with a wash solution comprising one or more surfactants. In some aspects, the protein A purification does not comprise washing a protein A support with a wash solution comprising one or more surfactants.

In some aspects, the wash solution clears virus as measured by a LRV.

In some aspects, a protein purification method comprises a) loading a mixture comprising a protein of interest and one or more contaminants, aggregates and/or viruses onto a protein A chromatography support, b) washing the support with a protein A chromatography wash solution comprising one or more surfactants to remove the one or more contaminant proteins, aggregates and/or viruses from the protein A chromatography support, c) eluting the protein of interest from the protein A chromatography support, d) loading the eluate comprising the protein of interest onto a cation exchange (CEX) chromatography support, e) washing the CEX chromatography support with a CEX chromatography wash solution comprising one or more surfactants to remove the one or more contaminant proteins, aggregates and/or viruses from the support, and f) eluting the protein of interest from the CEX chromatography support, thereby forming a purified eluate of the protein of interest.

In some aspects, the contaminant proteins are host cell proteins. In some aspects, the host cell proteins are derived from Chinese hamster ovary cells.

In some aspects, the protein A wash solution clears virus as measured by log reduction value (LRV). In some aspects, the CEX wash solution clears viral as measured by a LRV.

In some aspects, the LRV is between about 1.0 and about 10.0 $\log_{10}$. In some aspects, the LRV is between about 1.0 and about 5.0 $\log_{10}$. In some aspects, the LRV is between about 4.0 and about 8.0 $\log_{10}$. In some aspects, the LRV is about a 3.0 $\log_{10}$. In some aspects, the LRV is about 4.0 $\log_{10}$. In some aspects, the LRV is about 5.0 $\log_{10}$. In some aspects, the LRV is about 6.0 $\log_{10}$.

In some aspects, the LRV is measured by quantitative PCR. In some aspects, the LRV is measured using an infectivity assay.

In some aspects, the LRV is achieved by applying 1 column volume (CV) of the wash. In some aspects, the LRV is achieved by applying 2 CVs of the wash. In some aspects, the LRV is achieved by applying 3 CVs of the wash. In some aspects, the LRV is achieved by applying 4 CVs of the wash. In some aspects, the LRV is achieved by applying 5 CVs of the wash.

In some aspects, the method further comprises applying a wash solution that does not comprise a surfactant to the support prior to applying the wash solution comprising the one or more surfactants to the support.

In some aspects, the method further comprises treating the purified eluate of the protein of interest with diafiltration, ultrafiltration, or both diafiltration and ultrafiltration.

In some aspects, the method further comprises loading the purified eluate of the protein of interest onto a membrane chromatography support and collecting flow through comprising a further-purified eluate from the membrane chromatography support.

In some aspects, the method does not comprise an anion exchange chromatography step.

In some aspects, the method further comprises subjecting the eluate to a viral inactivation step. In some aspects, the viral inactivation is achieved by low pH viral inactivation to form a virally-inactivated preparation. In some aspects, the pH is lowered to between about 2.5 to and about 5. In some aspects, the method further comprises lowering the pH of the purified eluate of the protein of interest for a period of time sufficient to inactivate viruses.

In some aspects, the method further comprises filtering the purified eluate of the protein of interest to remove viruses.

In some aspects, the method further comprises formulating the purified eluate of the protein of interest as a composition including a pharmaceutically acceptable excipient.

In some aspects, the method further comprises expressing the protein of interest and one or more contaminant proteins in a bioreactor having a capacity of at least about 250 liters. In some aspects, the bioreactor has a capacity of at least about 500 liters, at least about 2000 liters, or at least about 5000 liters.

In some aspects, the protein of interest comprises an antibody or antigen binding fragment thereof, or fusion protein construct thereof. In some aspects, the antibody or antigen binding fragment thereof (a) specifically binds to TNF-like ligand 1A (TL1a), optionally wherein the antibody or antigen binding fragment thereof comprises a VH comprising the amino acid sequence of SEQ ID NO: 5 or 6 and a VL comprising the amino acid sequence of SEQ ID NO: 7 (b) specifically binds to calcitonin gene-related peptide (CGRP), optionally wherein the antibody or antigen binding fragment thereof comprises a VH comprising the amino acid sequence of SEQ ID NO: 1 and a VL comprising the amino acid sequence of SEQ ID NO: 2 or (c) specifically binds to CD38, optionally wherein the antibody or antigen binding fragment thereof comprises a VH comprising the amino acid sequence of SEQ ID NO: 3 and a VL comprising the amino acid sequence of SEQ ID NO: 4.

In some aspects, provided herein is a use of a wash solution during cation exchange (CEX) chromatography for purifying a protein of interest bound to a CEX support, wherein the wash solution comprises one or more surfactants.

In some aspects, provided herein is a cation exchange (CEX) chromatography wash solution for purifying a protein of interest bound to a CEX support, comprising surfactant.

In some aspects of a use, method, or wash provided herein, the protein A chromatography wash solution or the CEX chromatography wash solution comprises about 0.1% to about 0.6% w/v of the surfactant. In some aspects, the protein A chromatography wash solution or the CEX chromatography wash solution comprises about 0.2% to about 0.5% w/v of the surfactant. In some aspects, the protein A chromatography wash solution or the CEX chromatography wash solution comprises about 0.2% w/v of the surfactant. In some aspects, the protein A chromatography wash solution or the CEX chromatography wash solution comprises about 0.3% w/v of the surfactant. In some aspects, the protein A chromatography wash solution or the CEX chromatography wash solution comprises about 0.5% w/v of the surfactant. In some aspects, the wherein the protein A chromatography wash solution or the CEX chromatography wash solution comprises about 0.6% w/v of the surfactant.

In some aspects of a use, method, or wash provided herein, the surfactant is a non-ionic surfactant. In some aspects, the surfactant is TRITON® X-100. In some aspects, the wash comprises about 0.2% TRITON® X-100. In some aspects, the wash comprises about 0.5% TRITON® X-100. In some aspects, the surfactant is PS 80. In some aspects, the wash comprises about 0.3% PS 80. In some aspects, the wash comprises about 0.6% PS 80.

In some aspects of a use, method, or wash provided herein, the protein A chromatography wash solution or the CEX chromatography wash solution further comprises arginine, optionally wherein the protein A chromatography wash solution or the CEX chromatography wash solution comprises about 25 mM arginine. In some aspects, the protein A chromatography wash solution or the CEX chromatography wash solution further comprises histidine, optionally wherein the protein A chromatography wash solution or the CEX chromatography wash solution comprises about 5 mM histidine. In some aspects, the protein A chromatography wash solution or the CEX chromatography wash solution further comprises sodium chloride optionally, wherein the protein A chromatography wash solution or the CEX chromatography wash solution comprises about 5 mM to about 15 mM sodium chloride. In some aspects, the protein A chromatography wash solution or the CEX chromatography wash solution comprises about 10 mM sodium chloride or about 11 mM sodium chloride. In some aspects, the protein A chromatography wash solution or the CEX chromatography wash solution further comprises sodium phosphate, optionally wherein the protein A chromatography wash solution or the CEX chromatography wash solution comprises about 10 mM sodium phosphate. In some aspects, the protein A chromatography wash solution or the CEX chromatography wash solution further comprises sodium acetate, optionally wherein the protein A chromatography wash solution or the CEX chromatography wash solution comprises about 20 mM to about 50 mM sodium acetate. In some aspects, the protein A chromatography wash solution or the CEX chromatography wash solution comprises about 25 mM sodium acetate or about 50 mM sodium acetate.

In some aspects of a use, method, or wash provided herein, the protein A chromatography wash solution or the CEX chromatography wash solution comprises, (a) about 10 mM sodium phosphate and about 0.2% TRITON® X-100, (b) about 10 mM sodium phosphate and about 0.5% TRITON® X-100, (c) about 10 mM sodium phosphate and about 0.3% PS 80, or (d) about 10 mM sodium phosphate and about 0.6% PS 80. In some aspects, the protein A chromatography wash solution or the CEX chromatography wash solution comprises (a) about 50 mM sodium acetate, about 25 mM arginine, about 5 mM histidine, about 11 mM sodium chloride and about 0.3% PS 80, (b) about 50 mM sodium acetate, about 25 mM arginine, about 5 mM histidine, about 11 mM sodium chloride and about 0.6% PS 80, (c) about 50 mM sodium acetate, about 25 mM arginine, about 5 mM histidine, about 11 mM sodium chloride and about 0.2% TRITON® X-100, (d) about 50 mM sodium acetate, about 25 mM arginine, about 5 mM histidine, about 11 mM sodium chloride and about 0.5% TRITON® X-100, (e) about 25 mM sodium acetate, about 10 mM sodium chloride and about 0.3% PS 80, (f) about 25 mM sodium acetate, about 10 mM sodium chloride and about 0.6% PS 80, (g) about 25 mM sodium acetate, about 10 mM sodium chloride and about 0.2% TRITON® X-100, or (h) about 25 mM sodium acetate, about 10 mM sodium chloride and about 0.5% TRITON® X-100.

In some aspects of a use, method, or wash provided herein, the protein A chromatography wash solution or the CEX chromatography wash solution comprises a pH of about 5.0 to 7.0. In some aspects, the protein A chromatography wash solution or the CEX chromatography wash solution comprises a pH of about 5.5 or about 6.3.

In some aspects, provided herein is a preparation of a protein of interest produced by any method provided herein. In some aspects, provided herein is a virus-inactivated preparation of a protein of interest, produced by any method provided herein. In some aspects, the protein of interest is an antibody or antigen binding fragment thereof. In some aspects, the antibody or antigen binding fragment thereof (a) specifically binds to TNF-like ligand 1A (TL1a), optionally wherein the antibody or antigen binding fragment thereof comprises a VH comprising the amino acid sequence of SEQ ID NO: 5 or 6 and a VL comprising the amino acid sequence of SEQ ID NO: 7, (b) specifically binds to calcitonin gene-related peptide (CGRP), optionally wherein the antibody or antigen binding fragment thereof comprises a VH comprising the amino acid sequence of SEQ ID NO: 1 and a VL comprising the amino acid sequence of SEQ ID NO: 2, or (c) specifically binds to CD38, optionally wherein the antibody or antigen binding fragment thereof comprises a VH comprising the amino acid sequence of SEQ ID NO: 3 and a VL comprising the amino acid sequence of SEQ ID NO: 4.

In some aspects, provided herein is a composition comprising a preparation of a protein of interest produced by any method provided herein and a pharmaceutically acceptable excipient. In some aspects, provided herein is a composition comprising a virus-inactivated preparation of a protein of interest and a pharmaceutically acceptable excipient, produced by any method provided herein.

In some aspects, provided herein is a composition comprising an aqueous carrier and a recombinantly-expressed or hybridoma-expressed antibody or antigen-biding fragment thereof, wherein the composition is substantially free of viral particles, and wherein the antibody or antigen-binding fragment thereof (a) specifically binds to TNF-like ligand 1A (TL1a) and comprises one or more complementary determining regions (CDRs) of a VH comprising the amino acid sequence of SEQ ID NO: 5 or SEQ ID NO: 6 and one or more CDRs of a VL comprising the amino acid sequence of SEQ ID NO: 7 (b) specifically binds to calcitonin gene-related peptide (CGRP) and comprises one or more CDRs of a VH comprising the amino acid sequence of SEQ ID NO: 1 and one or more CDRs of a VL comprising the amino acid sequence of SEQ ID NO: 2, or (c) specifically binds to CD38, comprising one or more CDRs of a VH comprising the amino acid sequence of SEQ ID NO: 3 and one or more CDRs of a VL comprising the amino acid sequence of SEQ ID NO: 4. In some aspects, the composition is free of viral particles. In some aspects, the antibody or antigen-binding fragment thereof (a) comprises a VH comprising the amino acid sequence of SEQ ID NO: 5 or 6 and a VL comprising the amino acid sequence of SEQ ID NO: 7, (b) comprises a VH comprising the amino acid sequence of SEQ ID NO: 1 and a VL comprising the amino acid sequence of SEQ ID NO: 2, or (c) comprises a VH comprising the amino acid sequence of SEQ ID NO: 3 and a VL comprising the amino acid sequence of SEQ ID NO: 4.

In some aspects, provided herein is a composition comprising an aqueous carrier and a recombinantly-expressed or hybridoma-expressed antibody prepared by a method comprising: a) loading a mixture comprising the antibody and one or more contaminants, aggregates and/or viruses onto a protein A chromatography support, b) washing the support with a protein A chromatography wash solution comprising one or more surfactants to remove the one or more contaminant proteins, aggregates and/or viruses from the protein A chromatography support, c) eluting the antibody from the protein A chromatography support, d) loading the eluate from step c) onto a cation exchange (CEX) chromatography support, e) washing the CEX chromatography support with a CEX chromatography wash solution comprising one or more surfactants to remove the one or more contaminant proteins, aggregates and/or viruses from the support, and f) eluting the antibody from the CEX chromatography support, thereby forming a purified eluate of the antibody. In some aspects, the antibody or antigen-binding fragment thereof (a) specifically binds to TNF-like ligand 1A (TL1a) and comprises one or more complementary determining regions (CDRs) of a VH comprising the amino acid sequence of SEQ ID NO: 5 or SEQ ID NO: 6 and one or more CDRs of a VL comprising the amino acid sequence of SEQ ID NO: 7, (b) specifically binds to calcitonin gene-related peptide (CGRP) and comprises one or more CDRs of a VH comprising the amino acid sequence of SEQ ID NO: 1 and one or more CDRs of a VL comprising the amino acid sequence of SEQ ID NO: 2, or (c) specifically binds to CD38 and comprises one or more CDRs of a VH comprising the amino acid sequence of SEQ ID NO: 3 and one or more CDRs of a VL comprising the amino acid sequence of SEQ ID NO: 4. In some aspects, the composition is substantially free of viral particles. In some aspects, the composition has not been subjected to anion exchange chromatography prior to the CEX chromatography. In some aspects, the composition has not been subjected to any ion exchange chromatography prior to the CEX chromatography.

BRIEF DESCRIPTION OF THE DRAWINGS

FIG. 1 is a schematic diagram of an exemplary protein purification process using the methods provided herein. As demonstrated in the working examples, the "surfactant wash" can substantially remove virus particles and can also increase yield as compared to using a wash that does not contain surfactant. "Wash 3," an intermediate wash step can remove surfactant, thereby increasing yield as compared to a process that does not include a wash step to remove surfactant and instead requires discarding an initial elution fraction that contains surfactant. The methods shown in this schematic can be used without a protein A purification step or in combination with (e.g., downstream of) a protein purification A purification step.

DETAILED DESCRIPTION OF THE INVENTION

It has been observed in accordance with the disclosure that the inclusion of surfactant in a CEX wash solution substantially enhances viral clearance from a protein preparation during CEX chromatography purification. This is advantageous because it makes possible the omission of an AEX chromatography step in the protein purification method. Surprisingly, it was found that the surfactant did not have a detrimental effect on the protein of interest. Moreover, it was found that the CEX wash solution increased the removal of host cell proteins from the protein preparation. It was also found that the use of an intermediate wash, after the surfactant-containing wash, but prior to elution of the protein from the CEX chromatography support, surprisingly improves the yield of protein of interest in the eluate and improves HCP clearance, in addition to removing any residual surfactant from the CEX chromatography support.

The level of HCP removal and viral clearance was observed to be so substantial that subsequent purification steps with anion exchange (AEX) chromatography could be removed from the protein purification scheme. Thus, in one embodiment, the protein purification methods described herein do not comprise an AEX step. Such a protein purification method may comprise an affinity chromatography step, followed by a CEX chromatography step as described herein.

The disclosure features affinity and CEX chromatography wash compositions, protein purification schemes that utilize such compositions, and protein preparations having a high degree of purity, for example, as having been purified with the use of such compositions or purification schemes. The compositions and purification schemes are particularly well-suited for hybridoma- or recombinantly-expressed monoclonal antibodies, but may also be used in the preparation of any recombinantly expressed proteins purified by CEX chromatography.

Accordingly, provided herein are affinity and cation exchange chromatography wash compositions, polypeptide purification schemes that utilize such compositions, and polypeptide preparations having a high degree of purity, for example, as having been purified with the use of such compositions or purification schemes.

I. Definitions

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The term "a solution comprising water" is used interchangeably with the term "an aqueous solution."

The terms "host cell proteins," "HCP," "host cell protein contaminants" and "host cell protein impurities" are used interchangeably herein.

The terms "polypeptide," "peptide," "polypeptide of interest", and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains. Preferably, the protein of interest is a polypeptide, an antibody or antigen binding fragment thereof, or an antibody construct.

The term "anti-TNF-like ligand 1A (TL1a)" refers to any protein capable of binding to TL1a. Anti-TL1a proteins include, for example anti-TL1a antibodies or antigen-binding fragments thereof. The antibody may be any antibody described in U.S. Publ. No. 2014/0255302, which is incorporated by reference herein. The antibody may be any antibody described in U.S. Provisional Application. No. 62/220,442.

The term "anti-calcitonin gene-related peptide (CGRP)" refers to any protein capable of binding to CGRP. Anti-GCRP proteins include, for example anti-CGRP antibodies or antigen-binding fragments thereof. The antibody may be any antibody described in U.S. Publ. No. 2009/0220489 or PCT Publ. No. WO 2007/054809.

The term "anti-CD38" refers to any protein capable of binding to CD38. Anti-CD38 proteins include, for example anti-CD38 antibodies or antigen-binding fragments thereof. The antibody may be any antibody described in U.S. Publ.

No. 2016/0068612 or in U.S. Publ. No. 2015/0313965, each of which are incorporated by reference herein, including antibodies that are further fused to an attenuated interferon molecule as described in these publications.

As used herein, the terms "antibody" and "antibodies" are terms of art and can be used interchangeably herein and refer to a molecule with an antigen-binding site that specifically binds an antigen.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. As used herein, the term "antibody" encompasses bispecific and multispecific antibodies.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies. An "antigen-binding fragment" can be a bispecific or multispecific antigen-binding fragment.

The term "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, the Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91(3):969-973 (1994), and Roguska et al., Protein Eng. 9(10):895-904 (1996). In some embodiments, a "humanized antibody" is a resurfaced antibody.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). In addition, combinations of these two approaches are sometimes used in the art to determine CDRs.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "hybridoma-expressed" refers to a protein of interest that is expressed in a hybrid cell line produced by the fusion of an immortal cell line of immunologic origin and an antibody producing cell. The term "hybridoma" encompasses progeny of heterohybrid myeloma fusions, which are the result of a fusion with human cells and a murine myeloma cell line subsequently fused with a plasma cell, commonly known as a trioma cell line. Furthermore, the term "hybridoma" is meant to include any immortalized hybrid cell line that produces antibodies such as, for example, quadromas (See, for example, Milstein et al., 1983, Nature, 537:3053). The hybrid cell lines can be of any species, including human and mouse.

The term "recombinantly-expressed" refers to a protein of interest is expressed in a "recombinant host cell" that has been genetically altered, or is capable of being genetically altered, by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell" as used herein.

The term "amino acid" refers to any naturally-occurring and/or non-natural amino acid residue. The term "naturally-occurring amino acid" refers to Ala, Arg, Asn, Asp, Cys, Glu, Gln, Gly, His, Ile, Leu, Lys, Met, Phe, Pro, Ser, Thr, Trp, Tyr, and Val. The term "basic amino acid" refers to arginine, lysine, glycine and histidine. Amino acids also include the D-forms of natural and non-natural amino acids. "D-" designates an amino acid having the "D" (dextrorotary) configuration, as opposed to the configuration in the naturally occurring ("L-") amino acids. Natural and non-natural amino acids can be purchased commercially (Sigma Chemical Co., Advanced Chemtech) or synthesized using methods known in the art.

The term "viral clearance" is used interchangeably with the terms "virus removal," and "removal of viruses". The term "viral inactivation" refers to rendering a virus contained in the mixture nonfunctional. The virus may originate from the source of antibody production, downstream processing steps or manufacturing conditions. Methods of rendering a virus nonfunctional or removing a virus include heat activation, pH inactivation, chemical inactivating agents, etc. The term "pH viral inactivation" includes subjecting a virus to a pH sufficient to render the virus nonfunctional, e.g. a pH between about 2.5 and 5.0.

The terms "$\log_{10}$ reduction factor (LRF)," "$\log_{10}$ reduction value (LRV)," and "log clearance" are interchangeable and refer to the calculated ratio of the viral titer in the starting material and in the relevant product fraction. The reduction factor is a suitable parameter to describe the potential or capacity of a process step to remove or inactivate viruses. LRV of any process step can be measured using any known model virus that resembles viruses which may contaminate the product, e.g. murine leukemia virus (MuLV) and minute virus of mice (MVM). LRV can also be measured by retroviral like particles (RVLP). LRV can be calculated by quantitative PCR (qPCR) or using an infectivity assay (e.g., measuring $TCID_{50}$.)

The invention provides for a purified eluate and a composition comprising a protein of interest that is "substantially free" of viral particles as measured by viral clearance studies using any of the methods of the invention. As used herein, the term "substantially free of viral particles" refers to a purified eluate or composition comprising a protein of interest in which the protein of interest has been separated from viral particles. The term "substantially free" refers to a solution or composition comprising the protein of interest having less than about 0.0005% to about 0.001% viral particles. Preferably, the composition is "substantially free" when the composition has less than about 0.0005% viral particles.

The invention provides for a purified eluate and a composition comprising a protein of interest that is "free" of viral particles as measured by viral clearance studies using any of the methods of the invention. As used herein, the term "free of viral particles" refers to a composition having less than about 0.0001%. The composition is free of viral particles when the viral particles cannot be detected by viral clearance studies under conditions of maximum sensitivity.

The terms "column," "support," "ligand," and "resin" are used interchangeably herein.

The terms "composition" and "purified composition" are interchangeable and refer to compositions including a carrier and the polypeptide of interest. The carrier is preferably aqueous, and may be a pharmaceutically acceptable carrier. The carrier may comprise a buffer, and may comprise one or more pharmaceutically acceptable excipients. The composition may be referred to as a pharmaceutical composition.

The term "affinity chromatography" or "affinity purification" refers to a separation method based on a specific binding interaction between an ligand immobilized or coupled to a solid support and its binding partner. When a complex mixture is passed over the column, those molecules having specific binding affinity to the ligand become bound. After other sample components are washed away, the bound molecule is stripped form the support, resulting in its purification from the original mixture. Each specific affinity system requires its own set of conditions known to a person of ordinary skill in the art.

The term "affinity ligand" refers to metals (e.g., Cd+2, Co+2, Cu+2, Ga+3, Fe+3, Ni+2, and Zn+2), dyes (e.g., Cibacron Blue and variants thereof), glutathione, subtilisin, Protein A, Protein G, Protein A/G, Protein L, boronate, avidin, streptavidin, biotin, anti-c-Myc, anti-HA, nucleotides, coenzymes, antibodies, heparin, antigens (especially for antibodies with a known specificity), and other known affinity ligands.

II. Compositions Comprising Proteins of Interest and Preparation Thereof for Purification As demonstrated herein, methods of purifying proteins can be improved through the use of a surfactant-containing wash (e.g., a CEX chromatography column wash). The methods can be used to capture and purify recombinantly expressed proteins, e.g., directly from a harvest cell culture fluid (HCCF). The methods can also be used to further purify (polish) recombinantly expressed proteins, e.g., proteins that have already been partially purified from a HCCF (e.g., via protein A purification).

In some embodiments, the proteins of interest preferably comprise antibodies or antigen-binding fragments thereof. In some embodiments, the protein of interest is an antibody that specifically binds to TNF-like ligand 1A (TL1a). An antibody that specifically binds to TL1a may comprise a heavy chain variable region (VH) comprising the amino acid sequence of SEQ ID NO: 5 or SEQ ID NO: 6 (or a sequence having 90%, 95%, or 99% identity thereto) and a light chain variable region (VL) comprising the amino acid sequence of SEQ ID NO: 7 (or a sequence having 90%, 95%, or 99% identity thereto). In some embodiments, the protein of interest is an antibody that specifically binds to calcitonin gene-related peptide (CGRP). An antibody that specifically binds to CGRP may comprise a VH comprising the amino acid sequence of SEQ ID NO: 1 (or a sequence having 90%, 95%, or 99% identity thereto) and a VL comprising the amino acid sequence of SEQ ID NO: 2 (or a sequence having 90%, 95%, or 99% identity thereto). In some embodiments, the protein of interest is an antibody that specifically binds to CD38. An antibody that specifically binds to CD38 may comprise a VH comprising the amino acid sequence of SEQ ID NO: 3 (or a sequence having 90%, 95%, or 99% identity thereto) and a VL comprising the amino acid sequence of SEQ ID NO: 4 (or a sequence having 90%, 95%, or 99% identity thereto). An antibody that specifically binds to CD38 may further comprise a fusion to an interferon molecule, including an interferon alpha molecule, and including an attenuated interferon alpha molecule.

The expression of a protein of interest may be carried out in any suitable host cell, which may be transformed with a gene encoding the protein. Host cells may be eukaryotic or prokaryotic, and include without limitation, bacteria cells, yeast cells, insect cells, and mammalian cells. Mammalian cells are preferred. Non-limiting examples of suitable mammalian cells include antibody-expressing hybridoma cells, as well as expression hosts such as Chinese Hamster Ovary (CHO) cells, human embryonic kidney 293 (HEK 293) cells, and murine hybridoma NS0 cells. The expressed polypeptide may be secreted from the cell to the cell culture media, or may be within the cell. The cell culture may be in a bioreactor (e.g., fermentation). Typical bioreactor cell cultures are initiated with a basal medium, with nutrients periodically infused after culture initiation and until the completion of the culture. This infusion is generally of a feed medium, and sustains the cell culture during the protein expression phase. For the most part, feed medium infusion is carried out via a bolus infusion, with concentrated feed medium quickly added into the cell culture at set time points, usually once per day. Alternatively to a bolus feed, bioreactor cell cultures may be infused using an extended or a continuous feed. Commercially available feed media are suitable for bioreactor nutrient infusion.

The bioreactor may have a capacity of at least about 250 liters. In some aspects, the bioreactor has a capacity of at least about 500 liters. In some aspects, the bioreactor has a capacity of at least about 2000 liters. In some aspects, the bioreactor has a capacity of at least about 5000 liters, or 10,000 liters or 15,000 liters.

Following expression, the media containing the polypeptide (e.g., cell culture media) may be clarified, for example, to remove the host cells and particulate debris. Clarification may comprise filtration, centrifugation, or a combination thereof. For example, depth filtration through diatomaceous earth and cellulose fibers may be used. Membrane filtration, using any commercially available membrane filter, for example, through a 0.2 µm filter may be employed to remove any microbial contaminants.

Following expression, and clarification if employed, the polypeptide of interest may be purified via affinity chromatography to remove contaminating host cell proteins (HCPs). Affinity chromatography may include any affinity ligands suitable for purification of the polypeptide of interest. Non-limiting examples of affinity chromatography ligands include metals (e.g., $Cd^{+2}$, $Co^{-2}$, $Cu^{+2}$, $Ga^{+3}$, $Fe^{+3}$, $Ni^{+2}$, and $Zn^{+2}$), dyes (e.g., Cibacron Blue and variants thereof), glutathione, subtilisin, Protein A, Protein G, Protein A/G, Protein L, boronate, avidin, streptavidin, biotin, anti-c-Myc, anti-HA, nucleotides, coenzymes, antibodies, heparin, antigens (esp. for antibodies with a known specificity), and other known affinity ligands. The affinity ligand is generally immobilized on a solid support, for which there are numerous known and common supports. In an embodiment of the present invention, CEX chromatography with the wash solutions described herein may replace the step of affinity chromatography. In this embodiment, following expression, and clarification if employed, an aqueous solution comprising the polypeptide of interest may be loaded onto the CEX support, without prior affinity chromatography.

III. CEX Purification

Following affinity chromatography (when employed) the protein preparation is loaded onto the CEX support, whereby the protein of interest binds to the support. The support preferably has a high protein-binding capacity. The support is preferably equilibrated prior to loading with the polypeptide preparation. Equilibration is preferably with a buffer solution.

In some embodiments, the CEX support is a sepharose matrix resin. In some embodiments, the CEX support is a synthetic polymer matrix resin. Exemplary CEX supports include GE Capto S, Millipore Fractogel EMD SO3-, Fractogel EMD TMAE, Fractogel EMD, Eshnumo S, Eshmuno HCX, Tosoh Toyopearl CM, Tosoh Toyopearl SP, and Biorad Nuvia cPrime.

In some embodiments, the CEX support is a sepharose-based sulphopropyl strong cation exchange. The CEX support can be, for example, an SPFF resin.

In some embodiments, the CEX support comprises a cross-linked poly (styrenedivinylbenzene) polymer matrix with sulfopropyl ligand. The CEX support can be, for example, a Poros XS resin.

In some embodiments, the CEX support is a polymeric ion-exchange chromatography resin (Poros™ XS, Life Technologies Corp., Carlsbad, Calif.).

In some embodiments, the CEX support is 6% agarose beads crosslinked with quaternary ammonium (Q) strong anion exchange groups (Q Sepharose® Fast Flow, GE-Healthcare, Pittsburgh, Pa.).

Loading of the polypeptide preparation onto the CEX chromatography support is carried out at a temperature, in a volume, and for a time suitable to allow adsorption of the polypeptide of interest to the support. Undesired HCPs and viruses that do not bind to the support flow through the support during chromatography. The wash solutions described and exemplified herein are used to wash a CEX chromatography support toward the removal of contaminants, including viruses, aggregates and HCP. Following washing with an intermediate wash buffer, the protein of interest is eluted from the CEX support. The elution buffer is generally tailored to the type of CEX support and polypeptide of interest, and accordingly, may vary. Elution may be carried out at a temperature, in a volume, and for a time suitable to allow for maximal elution yield of the protein of interest. Elution of the protein produces a CEX chromatography eluate comprising the protein. Elution of the antibody or antibody construct produces a CEX eluate comprising the antibody or an antibody construct.

As well as reducing the HCP and aggregate content, the CEX chromatography wash solutions of the invention may be used to reduce the level of viruses or to inactivate viruses in the composition containing the protein of interest. Typical prior art purification processes use anion exchange followed by a further acidification treatment to reduce the level of viruses or to inactivate viruses during protein (e.g. antibody) purification methods. Surprisingly, the present inventors have found that use of a CEX chromatography wash solution of the present invention reduces the level of viruses sufficiently to omit the step of anion exchange chromatography or viral inactivation step.

IV. Viral Clearance Using Surfactant Washes and Other Methods

Prior to loading the protein onto a CEX chromatography support, the protein solution (e.g., comprising the polypeptide or comprising the antibody or antibody construct) may be further treated with a treatment to inactivate any residual viruses present in the eluate. The virus inactivation may comprise acidifying the eluate at a temperature and for a period of time sufficient to inactivate any viruses present in the eluate. The acidification may comprise, for example, adding acetic acid, citric acid, hydrochloric acid, formic acid, phosphoric acid, caprylic acid, other suitable acids, or a combination thereof to the eluate until a desired pH is achieved. After low pH viral inactivation, the eluate may be neutralized to pH 3.0 to 7.5 (depending on process needs). In some embodiments the eluate is neutralized to a pH of about 3.0 to about 3.5, a pH of about 3.0 to about 4.0, a pH of about 3.5 to about 4.5, a pH of about 4.0 to about 5.5, a pH of about 4.5 to 5.5, a pH of about 6.0 to about 7.0, or a pH of about 6.0 to about 7.5. In some embodiments the eluate is neutralized to a pH of about 3.0, a pH of about 3.5, a pH of about 4.0, a pH of about 4.5, a pH of about 5.0, a pH of about 5.5, a pH of about 6.0, a pH of about 6.5, a pH of about 7.0 or a pH of about 7.5. During the neutralization step, turbidity may appear in the product pool due to precipitation of impurities (or product). Depth filtration may be used to filter the pH-adjusted preparation to remove turbidity as well as impurities.

The unit operation of inactivating viruses present in a fluid comprising the protein of interest can be performed in a holding tank that is capable of incubating a fluid comprising the recombinant therapeutic protein at a pH of between about 2.5 to 5.0, between about 3.5 to about 4.5, between about 3.5 to about 4.25, between about 3.5 to about 4.0, between about 3.5 to about 3.8, or about 3.75 for a period of at least 25 minutes, a period of between about 30 minutes to 1.5 hours, a period of between about 30 minutes to 1.25 hours, a period of between about 0.75 hours to 1.25 hours, or a period of about 1 hour.

In alternative embodiments, the viral inactivation step may be carried out using other methods known in the art. For example, the viral inactivation step may comprise, in various embodiments, treatment with acid, detergent, chemicals, nucleic acid cross-linking agents, ultraviolet light, gamma radiation, heat, or any other process known in the art to be useful for this purpose.

Viruses can be removed by filtration. For example, viral filtration can be performed before and/or after the step of flowing the recombinant protein through a depth filter. Viruses can be removed from a solution comprising recombinant protein by either a normal flow filter (NFF) or a tangential flow filtration (TFF) filter such as is described in U.S. Pat. No. 6,365,395. In either TFF mode or NFF mode, filtration is conducted under conditions to retain the virus, generally having a 20 to 100 nanometer (nm) diameter, on the membrane surface while permitting passage of the recombinant protein through the membrane.

The objective of viral clearance studies is to assess the process step(s) that can be considered to be effective in inactivating/removing viruses and to estimate quantitatively the overall level of virus reduction obtained by the process step(s). The level of virus reduction may be obtained by the addition ("spiking") of significant amounts of virus to the mixture containing the protein of interest, obtained after various process steps, and then demonstrating the removal or inactivation of the virus during subsequent steps. The reduction of virus infectivity may be achieved by the removal of virus particles or the inactivation of viral infectivity. Viral clearance studies are performed to demonstrate the clearance of a virus known to be present in the mixture. Reduction factors are normally expressed on a logarithmic scale ($\log_{10}$). Model viruses for clearance evaluation studies are chosen to resemble viruses which may contaminate the mixture containing the protein of interest. Model viruses, such as xenotropic murine leukemia virus (X-MulV) and minute virus of mice (MVM), are often used for the viral clearance validation of cell line-derived proteins of interest.

In some embodiments, the CEX wash solution or the ProA wash solution increases viral clearance or inactivates viruses from a mixture containing the protein of interest. In some embodiments, the wash solution increases viral clearance during the protein A chromatography step. In some embodiments, the wash solution increases viral clearance during the CEX chromatography step. Viral clearance can be measured in $\log_{10}$ reduction values (LRV). In some embodiments, the wash solution increases viral clearance wherein the LRV is between about 1.0 and about 10.0 $\log_{10}$. In some embodiments, the wash solution increases viral clearance wherein the LRV is between about 1.0 and about 5.0 $\log_{10}$, the LRV is between about 1.0 and about 3.0 $\log_{10}$, the LRV is between about 2.0 and about 4.0 $\log_{10}$, the LRV is between about 3.0 and about 5.0 $\log_{10}$ or the LRV is between about 5.0 $\log_{10}$ and 6.0 $\log_{10}$. In some embodiments, the LRV is about 1.0 $\log_{10}$, the LRV is about 2.0 $\log_{10}$, the LRV is about 3.0 $\log_{10}$, the LRV is about 4.0 $\log_{10}$, the LRV is about 5.0 $\log_{10}$, the LRV is about 6.0 $\log_{10}$, the LRV is about 7.0 $\log_{10}$, the LRV is about 8.0 $\log_{10}$, the LRV is about 9.0 $\log_{10}$, or the LRV is about 10.0 $\log_{10}$. The LRV can be achieved by applying 1 column volume (CV) of the wash, 2 CVs of the wash, 3 CVs of the wash, 4 CVs of the wash, or 5 CVs of the wash.

V. Further Processing of Proteins Purified Using a Surfactant-Containing Wash and Compositions Produced Therefrom Following virus inactivation, or following elution from the CEX chromatography if virus inactivation is not included, the protein of interest may be further processed into a form suitable for therapeutic administration, for example, to an non-human animal or to a human being. Such further processing may include any combination of ultrafiltration, nanofiltration, concentration, and diafiltration of the purified preparation of the protein of interest.

Ultrafiltration is a process for concentrating the preparation of the protein of interest. Proteins are filtered from other molecules in solution based on the membrane pore size or molecular weight cutoff. Diafiltration is used to exchange the protein of interest into a desired buffer (e.g., from an elution buffer into a stable formulation buffer). Ultrafiltration and diafiltration typically employ tangential flow filtration.

Following a purification scheme, which includes the use of a CEX chromatography wash buffer of the present invention, the protein of interest is preferably present in a composition. The composition preferably includes a carrier and the protein of interest. The carrier is preferably aqueous, and may be a pharmaceutically acceptable carrier. The carrier may comprise a buffer, and may comprise one or more pharmaceutically acceptable excipients. The composition may be referred to as a pharmaceutical composition. The terms "composition" and "purified composition" are used interchangeably herein.

Compositions comprising purified proteins of interest, which proteins are, in some embodiments, purified according to the methods described or exemplified herein are provided. Such compositions comprise the protein of interest and a minimal amount of retro-viral like particles (RVLPs), the latter being co-expressed with the protein of interest but largely separated from the protein of interest via CEX chromatography using the wash solutions described herein.

In some aspects, the polypeptide of interest in the composition is an antibody or antibody construct. The antibody or antibody construct may have been expressed recombinantly by a transformed host cell (e.g., a host cell comprising a gene encoding the antibody or antibody construct), or may have been expressed via a hybridoma cell. The antibody or antibody construct may specifically bind to an epitope on human TNF-like ligand 1A (TL1a). The antibody or antibody construct may specifically bind to an epitope on human calcitonin gene-related peptide (CGRP). The antibody or antibody construct may specifically bind to an epitope on human CD38.

In some aspects, the composition comprises a purified antibody or antibody construct that specifically binds to CGRP and comprises a heavy chain variable region and a light chain variable region. The heavy chain variable region (VH) may comprise the amino acid sequence of SEQ ID NO: 1. The light chain variable region (VL) may comprise the amino acid sequence of SEQ ID NO: 2. The composition may comprise an antibody or antibody construct comprising a VH comprising the amino acid sequence of SEQ ID NO: 1 and a VL, which antibody or antibody construct specifically binds to CGRP. The composition may comprise an antibody or antibody construct comprising a VL comprising the amino acid sequence of SEQ ID NO: 2 and a VH, which antibody or antibody construct specifically binds to CGRP. The composition may comprise an antibody or antibody construct comprising a VH comprising the amino acid sequence of SEQ ID NO: 1 and a VL comprising the amino acid sequence of SEQ ID NO: 2, which antibody or antibody construct specifically binds to CGRP. The antibody may be any antibody described in U.S. Publ. No. 2009/0220489 or PCT Publ. No. WO 2007/054809.

In some aspects, the composition comprises a purified antibody or antibody construct that specifically binds to TL1a and comprises a heavy chain variable region and a light chain variable region. The antibody may be any antibody described in U.S. Publ. No. 2014/0255302, which is incorporated by reference herein. The antibody may be any antibody described in U.S. Provisional Application. No. 62/220,442.

In some aspects, the composition comprises a purified antibody or antibody construct that specifically binds to CD38 and comprises a heavy chain variable region and a light chain variable region. The anti-CD38 antibody may further be fused to a second polypeptide molecule, for example, fused to a polypeptide toxin, or fused to an interferon polypeptide such as interferon alpha. The heavy chain variable region (VH) may comprise the amino acid sequence of SEQ ID NO: 3. The light chain variable region (VL) may comprise the amino acid sequence of SEQ ID NO: 4. The composition may comprise an antibody or antibody construct comprising a VH comprising the amino acid sequence of SEQ ID NO: 3 and a VL, which antibody or antibody construct specifically binds to CD38. The composition may comprise an antibody or antibody construct comprising a VL comprising the amino acid sequence of SEQ ID NO: 4 and a VH, which antibody or antibody construct specifically binds to CD38. The composition may comprise an antibody or antibody construct comprising a VH comprising the amino acid sequence of SEQ ID NO: 3 and a VL comprising the amino acid sequence of SEQ ID NO: 4, which antibody or antibody construct specifically binds to CD38. The antibody may be any antibody described in U.S. Publ. No. 2016/0068612 or in U.S. Publ. No. 2015/0313965, each of which are incorporated by reference herein, including antibodies that are further fused to an attenuated interferon molecule as described in these publications.

In some aspects, the composition comprises a purified antibody or antibody construct that specifically binds to TL1a and comprises a heavy chain variable region and a light chain variable region. The VH may comprise the amino acid sequence of SEQ ID NO: 5. The VH may comprise the amino acid sequence of SEQ ID NO: 6. The VL may comprise the amino acid sequence of SEQ ID NO: 7. Thus, the VH may comprise SEQ ID NO: 5 and the VL may comprise SEQ ID NO: 7, or the VH may comprise SEQ ID NO: 6 and the VL may comprise SEQ ID NO: 7. The composition may comprise an antibody or antibody construct comprising a VH comprising the amino acid sequence of SEQ ID NO: 5 or SEQ ID NO: 6 and a VL, which antibody or antibody construct specifically binds to TL1a. The composition may comprise an antibody or antibody construct comprising a VL comprising the amino acid sequence of SEQ ID NO: 7 and a VH, which antibody or antibody construct specifically binds to TL1a. The composition may comprise an antibody or antibody construct comprising a VH comprising the amino acid sequence of SEQ ID NO: 5 or SEQ ID NO: 6 and a VL comprising the amino acid sequence SEQ ID NO: 7, which antibody or antibody construct specifically binds to TL1a. The antibody may be any antibody described in U.S. application Ser. No. 15/267,213 or U.S. Publ. No. 2014/0255302, each of which are incorporated by reference herein.

In some preferred aspects, the antibodies (e.g., anti-TL1a, anti-CGRP, and anti-CD38) comprise a human IgG constant region. The human IgG constant region may be a human IgG1 or a human IgG4 constant region. The antibodies (e.g., anti-TL1a, anti-CGRP, and anti-CD38) may be humanized antibodies or fully human antibodies.

VI. Wash Solutions

As provided herein, wash solutions comprising a surfactant can be used in methods of purifying proteins. Surfactant-containing wash solutions are surprisingly effective in removing viruses. Such washes can be used, for example, in cation exchange chromatography, which may or may not be proceeded by a protein A chromatography step. The protein A chromatography step can also use a surfactant-containing wash solution or can be performed with a wash that does not contain a surfactant.

The surfactant in the wash solution can be, for example a non-ionic surfactant. The surfactant in the wash solution can be, for example, a zwitterionic surfactant such as CHAPS (3-[(3-cholamidopropyl)dimethylammonio]-1-propane-sulfonate), CAHS (Cocamidopropyl hydroxysultaine) or SB-12 N-Dodecyl-N,N-dimethylammonio-3-propane sulfonate; a quaternary ammonium salt such as CTAB (Cetrimonium bromide) or DODAB (Dioctadecyldimethyl-ammonium bromide); an alkylphenol ethoxylate such as a nonoxynol (e.g., nonaethylene glycol); an ethoxylate; an alkyl polyglucoside such as Decyl glucoside, an amine or phosphine oxide; and/or an anionic surfactant such as SDS (Sodium dodecyl sulfate).

The surfactant in the wash solution can be, for example, Triton 100, nonyl phenoxypolyethoxylethanol (NP40), Sulfobetaine-12 (SB-12), Sulfobetaine-14 (SB-14), Lauryldimethylamine N-oxide (LDAO), polysorbate 20 (PS 20), polysorbate 80 (PS 80), or a combination thereof.

The surfactant in the wash solution can be, for example, Triton 100, NP 40, LDAO, SB-12, and/or SB-14.

In certain instances, the wash solution comprises a specified concentration of surfactant. The concentration of the surfactant in the wash solution can be, for example, about 0.01% to about 1% w/v. The concentration of the surfactant in the wash solution can be, for example, about 0.05% to about 1% w/v. The concentration of the surfactant in the wash solution can be, for example, about 0.1% to about 1% w/v. The concentration of the surfactant in the wash solution can be, for example, about 0.2% to about 1% w/v. The concentration of the surfactant in the wash solution can be, for example, about 0.5% to about 1% w/v.

The concentration of the surfactant in the wash solution can be, for example, about 0.01% to about 0.5% w/v. The concentration of the surfactant in the wash solution can be, for example, about 0.05% to about 0.5% w/v. The concentration of the surfactant in the wash solution can be, for example, about 0.1% to about 0.5% w/v. The concentration of the surfactant in the wash solution can be, for example, about 0.2% to about 0.5% w/v.

The concentration of the surfactant in the wash solution can be, for example about 0.01% w/v. The concentration of the surfactant in the wash solution can be, for example about 0.05% w/v. The concentration of the surfactant in the wash solution can be, for example about 0.1% w/v. The concentration of the surfactant in the wash solution can be, for example about 0.2% w/v. The concentration of the surfactant in the wash solution can be, for example about 0.5% w/v. The concentration of the surfactant in the wash solution can be, for example about 1% w/v.

In addition to the surfactant, the wash solution can comprise, for example, sodium acetate (e.g., at a concentration of 25 mM) and/or sodium chloride (e.g., at a concentration of 10 mM). Such a wash solution can, for example, have a pH of about 5.5.

In addition to the surfactant, the wash solution can comprise, for example sodium phosphate (e.g., at a concentration of 10 mM). Such a wash solution can, for example, have a pH of about 6.3.

In an embodiment, the wash solution comprises 10 mM sodium phosphate and 0.2% TRITON® X-100.

In an embodiment, the wash solution comprises 10 mM sodium phosphate and 0.5% TRITON® X-100.

In an embodiment, the wash solution comprises 10 mM sodium phosphate and 0.3% PS 80.

In an embodiment, the wash solution comprises 10 mM sodium phosphate and 0.6% PS 80.

In an embodiment, the wash solution comprises 10 mM sodium phosphate and 0.2% TRITON® X-100.

In an embodiment, the wash solution comprises 10 mM sodium phosphate and 0.5% TRITON® X-100.

In an embodiment, the wash solution comprises 10 mM sodium phosphate and 0.3% PS 80.

In an embodiment, the wash solution comprises 10 mM sodium phosphate and 0.6% PS 80.

In an embodiment, the wash solution comprises 50 mM sodium acetate, 25 mM arginine, 5 mM histidine, 11 mM sodium chloride and 0.3% PS 80.

In an embodiment, the wash solution comprises 50 mM sodium acetate, 25 mM arginine, 5 mM histidine, 11 mM sodium chloride and 0.6% PS 80.

In an embodiment, the wash solution comprises 50 mM sodium acetate, 25 mM arginine, 5 mM histidine, 11 mM sodium chloride and 0.2% TRITON® X-100.

In an embodiment, the wash solution comprises 50 mM sodium acetate, 25 mM arginine, 5 mM histidine, 11 mM sodium chloride and 0.5% TRITON® X-100.

In an embodiment, the wash solution comprises 25 mM sodium acetate, 10 mM sodium chloride and 0.3% PS 80.

In an embodiment, the wash solution comprises 25 mM sodium acetate, 10 mM sodium chloride and 0.6% PS 80.

In an embodiment, the wash solution comprises 25 mM sodium acetate, 10 mM sodium chloride and 0.2% TRITON® X-100.

In an embodiment, the wash solution comprises 25 mM sodium acetate, 10 mM sodium chloride and 0.5% TRITON® X-100.

In an embodiment, the disclosure features a CEX chromatography solution which comprises one or more surfactants. In some embodiments, the disclosure features a CEX chromatography wash solution, which comprises a basic amino acid, a salt, a non-ionic surfactant, or a buffer (e.g. an organic phosphate), and a surfactant. In some embodiments, the buffer is an is sodium phosphate and the non-ionic surfactant is 4-(1,1,3,3-Tetramethylbutyl)phenyl-polyethylene glycol (TRITON® X-100). In some embodiments, the buffer is an organic phosphate, optionally sodium phosphate, and the non-ionic surfactant is polysorbate 80 (PS 80). In some embodiments, the basic amino acid is arginine, the salt is sodium chloride, and the non-ionic surfactant is TRITON® X-100. In some embodiments, the non-ionic surfactant is TRITON® X-100 and the wash solution also comprises histidine. In some embodiments, the non-ionic surfactant is TRITON® X-100 and the wash solution also comprises histidine and sodium acetate. In some preferred embodiments, the buffer is sodium acetate, the salt is sodium chloride, and the non-ionic surfactant is TRITON® X-100. In some preferred embodiments, the buffer is sodium acetate, the salt is sodium chloride and the non-ionic surfactant is PS 80. In some embodiments, the wash solution has a pH range from about 5.0 to about 7.0. In an embodiment, the wash solution has a pH of about 5.0, a pH of about 5.5, a pH of about 6.0, a pH of about 6.5, or a pH of about 7.0. In one embodiment, the wash solution has a pH of about 6.3.

In some embodiments, the CEX wash solution or the ProA wash solution comprises greater than 0 mM and less than about 75 mM arginine, greater than 0 mM and less than about 30 mM sodium chloride, and greater than 5 mM and less than about 30 mM of an anionic surfactant. The wash solution may comprise from about 5 mM to about 10 mM arginine, from about 5 mM to about 15 mM arginine, from about 5 mM to about 20 mM arginine, from about 5 mM to about 25 mM arginine, from about 10 mM to about 30 mM arginine, from about 10 mM to about 40 mM arginine, from about 10 mM to about 50 mM arginine, from about 10 mM to about 60 mM arginine, from about 10 mM to about 75 mM arginine, from about 20 mM to about 50 mM arginine, or from about 20 mM to about 75 mM arginine. In some embodiments, the wash solution comprises about 5 mM arginine, about 10 mM arginine, about 15 mM arginine, about 20 mM arginine, about 25 mM arginine, about 30 mM arginine, about 40 mM arginine, about 50 mM arginine, about 60 mM arginine, or about 75 mM arginine. In some embodiments, the CEX wash solution or the ProA wash solution comprises greater than 0 mM and less than about 25 mM histidine, from about 5 mM to about 25 mM histidine, from about 5 mM to about 20 mM histidine, from about 10 mM to about 25 mM histidine, from about 10 mM to about 20 mM histidine. In some embodiments, the wash solution comprises about 5 mM histidine. In some embodiments, the wash solution comprises about 10 mM histidine, about 15 mM histidine, 20 mM histidine, or about 25 mM histidine.

In some embodiments, the CEX wash solution or the ProA wash solution comprises greater than 0 mM to about 100 mM sodium chloride, from about 10 mM to about 25 mM sodium chloride, from about 15 mM to about 25 mM sodium chloride, from about 25 mM to about 50 mM sodium chloride, from about 50 mM to 75 mM sodium chloride, or from about 75 mM to about 100 mM sodium chloride. In some embodiments, the wash solution comprises about 10 mM sodium chloride. In some embodiments, the wash solution comprises about 11 mM sodium chloride. In some embodiments, the wash solution comprises about 5 mM sodium chloride, about 15 mM sodium chloride, about 20 mM sodium chloride, about 25 mM sodium chloride, about 30 mM sodium chloride, about 35 mM sodium chloride, about 40 mM sodium chloride, about 45 mM sodium chloride, about 50 mM sodium chloride, about 55 mM sodium chloride, about 60 mM sodium chloride, about 65 mM sodium chloride, about 70 mM sodium chloride, about 75 mM sodium chloride, about 80 mM sodium chloride, about 85 mM sodium chloride, about 90 mM sodium chloride, about 95 mM sodium chloride, or about 100 mM sodium chloride.

In some embodiments, the CEX wash solution or the ProA wash solution may comprise from about 0.00% (w/v) to about 1.0% (w/v) of the non-ionic surfactant, from about 0.1% (w/v) to about 0.2% (w/v) of the non-ionic surfactant, from about 0.05% (w/v) to about 0.15% (w/v) of the non-ionic surfactant, from about 0.1% (w/v) to about 0.15% (w/v) of the non-ionic surfactant, from about 0.05% (w/v) to about 0.1% (w/v) of the non-ionic surfactant, or from about 0.1% (w/v) to about 0.5% (w/v) of the non-ionic surfactant, or from about 0.5% (w/v) to about 1.0% (w/v) of the non-ionic surfactant. In some embodiments, the wash solution comprises about 0.01% (w/v) of the non-ionic surfactant, about 0.05% (w/v) of the non-ionic surfactant, about 0.1% (w/v) of the non-ionic surfactant, about 0.15% (w/v) of the non-ionic surfactant, about 0.2% (w/v) of the non-ionic surfactant, about 0.25% (w/v). of the non-ionic surfactant, about 0.3% (w/v) of the non-ionic surfactant, about 0.35% (w/v) of the non-ionic surfactant, about 0.4% (w/v) of the non-ionic surfactant, about 0.45% (w/v) of the non-ionic surfactant, about 5.0% (w/v) of the non-ionic surfactant, about 0.55% (w/v) of the non-ionic surfactant, about 0.6% (w/v) of the non-ionic surfactant, about 0.65% (w/v) of the non-ionic surfactant, about 0.7% (w/v) of the non-ionic surfactant, about 0.75% (w/v) of the non-ionic surfactant, about 0.8% (w/v) of the non-ionic surfactant, about 0.85% (w/v) of the non-ionic surfactant, about 0.9% (w/v) of the non-ionic surfactant, about 0.95% (w/v) of the non-ionic surfactant, or about 1.0% (w/v) of the non-ionic surfactant. In some embodiments, the non-ionic surfactant comprises TRITON® X-100. In some embodiments, the non-ionic surfactant comprises PS 80. In some embodiments, the non-ionic surfactant is Lauryldimethylamine N-oxide (LDAO).

In some embodiments, the CEX wash solution or the ProA wash solution comprises greater than 0 mM to about 100 mM sodium acetate, from about 5 mM to about 20 mM sodium acetate, from about 5 mM to about 30 mM sodium acetate, from about 5 mM to about 40 mM sodium acetate, from about 5 mM to about 50 mM sodium acetate, from about 10 mM to about 25 mM sodium acetate, or from about 15 mM to about 30 mM sodium acetate, from about 20 mM to about 50 mM sodium acetate, from about 25 mM to about 40 mM sodium acetate, from about 35 mM to about 50 mM sodium acetate, from about 40 to about 65 mM sodium acetate, from about 45 mM to about 70 mM sodium acetate, from about 65 mM to about 80 mM sodium acetate, from about 75 mM to about 100 mM sodium acetate. In some embodiments, the wash solution comprises about 25 mM sodium acetate. In some embodiments, the wash solution comprises about 5 mM sodium acetate, about 10 mM sodium acetate, about 15 mM sodium acetate, about 20 mM sodium acetate, about 30 mM sodium acetate, about 35 mM sodium acetate, about 40 mM sodium acetate, about 45 mM sodium acetate, about 50 mM sodium acetate, about 55 mM sodium acetate, about 60 mM sodium acetate, about 65 mM sodium acetate, about 70 mM sodium acetate, about 75 mM sodium acetate, about 80 mM sodium acetate, about 85 mM sodium acetate, about 90 mM sodium acetate, about 95 mM sodium acetate, or about 100 mM sodium acetate.

In some embodiments, the CEX wash solution or the ProA wash solution comprises greater than about 0 mM to about 30 mM sodium phosphate. In a preferred embodiment, the wash solution comprises about 10 mM sodium phosphate. In some embodiments, the wash solution comprises from about 5 mM to about 10 mM sodium phosphate, from about 5 mM to about 15 mM sodium phosphate, from about 5 mM to 20 mM sodium phosphate, from about 10 mM to 25 mM sodium phosphate, or from about 10 mM to 30 mM sodium phosphate. In some embodiments, the wash solution comprises about 5 mM sodium phosphate, about 10 mM sodium phosphate, about 15 mM sodium phosphate, about 20 mM sodium phosphate, about 25 mM sodium phosphate or about 30 mM sodium phosphate.

In some embodiments the CEX wash solution or the ProA wash solution comprises greater than about 0 mM to about 100 mM sodium phosphate and greater than 0.0% to about 1.0% of non-ionic surfactant. In some embodiments, the wash solution comprises greater than 0 mM to about 100 mM sodium acetate, greater than 0 mM to about 100 mM sodium chloride, and greater than 0.0% to about 0 mM and less than about 500 mM arginine, greater than 0 mM to about 100 mM sodium chloride, greater than 0 mM and less than about 25 mM histidine, greater than 0 mM to about 50 mM sodium acetate, and greater than 0.0% to about 1.0% of non-ionic surfactant.

Any of the wash solutions of the invention may be used to purify proteins of interest using CEX chromatography supports.

In certain aspects, 1 to 10 column volumes (CVs) of the wash solution are applied to the CEX chromatography support. In certain aspects, 1 to 9 CVs of the wash solution are applied to the CEX chromatography support. In certain aspects, 1 to 8 CVs of the wash solution are applied to the CEX chromatography support. In certain aspects, 1 to 7 CVs of the wash solution are applied to the CEX chromatography support. In certain aspects, 1 to 6 CVs of the wash solution are applied to the CEX chromatography support. In certain aspects, 1 to 5 CVs of the wash solution are applied to the CEX chromatography support. In certain aspects, 1 to 4 CVs of the wash solution are applied to the CEX chromatography support. In certain aspects, 1 to 3 CVs of the wash solution are applied to the CEX chromatography support. In certain aspects, 1 to 2 CVs of the wash solution are applied to the CEX chromatography support.

In certain aspects, CV of the wash solution is applied to the CEX chromatography support. In certain aspects, 2 CVs of the wash solution are applied to the CEX chromatography support. In certain aspects, 3 CVs of the wash solution are applied to the CEX chromatography support. In certain aspects, 4 CVs of the wash solution are applied to the CEX chromatography support. In certain aspects, 5 CVs of the wash solution are applied to the CEX chromatography support.

In certain aspects of the methods provided herein, washing with a solution comprising a surfactant can be followed by washing with a solution that does not comprise a surfactant, e.g., before eluting a protein of interest. Washing with a solution that does not comprise a surfactant can remove surfactant. Washing with a solution to remove surfactant can increase yield, e.g., by eliminating the need to discard a first fraction of the elution because it contains surfactant, and has also been shown to improve the HCP clearance performance of the CEX chromatography.

In certain aspects, 1 to 10 column volumes (CVs) of the wash solution that does not comprise a surfactant are applied to the CEX chromatography support. In certain aspects, 1 to 9 CVs of the wash solution that does not comprise a surfactant are applied to the CEX chromatography support. In certain aspects, 1 to 8 CVs of the wash solution that does not comprise a surfactant are applied to the CEX chromatography support. In certain aspects, 1 to 7 CVs of the wash solution that does not comprise a surfactant are applied to the CEX chromatography support. In certain aspects, 1 to 6 CVs of the wash solution that does not comprise a surfactant are applied to the CEX chromatography support. In certain aspects, 1 to 5 CVs of the wash solution that does not comprise a surfactant are applied to the CEX chromatography support. In certain aspects, 1 to 4 CVs of the wash solution that does not comprise a surfactant are applied to the CEX chromatography support. In certain aspects, 1 to 3 CVs of the wash solution that does not comprise a surfactant are applied to the CEX chromatography support. In certain aspects, 1 to 2 CVs of the wash solution that does not comprise a surfactant are applied to the CEX chromatography support.

In certain aspects, CV of the wash solution that does not comprise a surfactant is applied to the CEX chromatography support. In certain aspects, 2 CVs of the wash solution that does not comprise a surfactant are applied to the CEX chromatography support. In certain aspects, 3 CVs of the wash solution that does not comprise a surfactant are applied to the CEX chromatography support. In certain aspects, 4 CVs of the wash solution that does not comprise a surfactant are applied to the CEX chromatography support. In certain aspects, 5 CVs of the wash solution that does not comprise a surfactant are applied to the CEX chromatography support.

In certain aspects of the methods provided herein, the washing with a solution comprising a surfactant is not followed by eluting a protein of interest without washing with a solution that does not comprise a surfactant before the elution. In such aspects, the first fraction of the elution, which may contain surfactant, can be discarded.

Embodiments of the present disclosure can be further defined by reference to the following non-limiting examples, which describe in detail preparation of wash solutions of the present disclosure and methods for using wash solutions of the present disclosure for the purification of proteins of interest. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

Example 1—Protein a Wash Solutions for Viral Clearance

Materials and Methods

Material and Equipment. Monoclonal antibodies used in these Examples were expressed using Chinese Hamster Ovary (CHO) cells. MABSELECT SURE® Protein A resin was purchased from GE Healthcare (Uppsala, Sweden). All buffer solutions were prepared using ultrapure water obtained from a Millipore water purification system. Chemicals used for buffer and solution preparation were obtained from JT Baker (Philipsburg, N.J.). All chromatographic experiments were carried out on anAkta Avant liquid chromatography system (GE Healthcare Life Sciences, Marlborough, Mass.). This instrument has a built-in UV- and conductivity monitoring system. Unicorn software (GE Healthcare Life Sciences, Marlborough, Mass.) was used for system control and sample collection.

Protein A Chromatography. The MABSELECT SURE® chromatography column was equilibrated with 1×PBS for 5 CV (column volume). After equilibration, the harvested cell culture fluid (HCCF) was loaded onto the column at a load capacity of 40 grams of mAb per liter of resin. Following load application, the column was first washed with 3 CV 1×PBS buffer, followed by a second wash with 5 CV of the candidate wash buffer. The column was subsequently washed with a third wash using 5 CV 5 mM succinic acid pH 5.8 buffer. The mAb was eluted from the column using 5CV 25 mM glycine, 10 mM succinic acid, pH 3.7 buffer. The cleaning in place was applied after production.

Quantitative ELISA-host cell protein (HCP). Host Cell Protein (HCP) was determined by the CHO Host Cell Proteins 3rd Generation kit (Immunoenzymetric Assay for the Measurement of CHO Host Cell Proteins, Catalog #F550, Cygnus Technologies, Southport, N.C.) following manufacturer's protocol. The absorbance data at 450/650 nm were acquired on the SPECTRAMAX® Plus microplate reader (Molecular Devices, Sunnyvale Calif.) and analyzed with SOFTMAX® Pro 6.4.2 software (Molecular Devices, Sunnyvale, Calif.). HCP values were calculated from a four parameter logistic fit of the standard curves generated from the standards included in the CHO Host Cell Proteins 3rd Generation kit.

Viral Clearance Results

Seven selected wash solutions were studied for RVLP clearance in a protein A chromatography wash, and the results are summarized in Table 1. TRITON® X-100 was highly effective in in vitro RVLP clearance.

TABLE 1

Retrovirus-Like Particle Clearance

| Wash Condition | Log10 Reduction Value (LRV) |
|---|---|
| 0.1% TRITON ® X-100 | 3.85 |
| 150 mM NaCl | 1.73 |
| 250 mM Arginine | 1.82 |
| 25 mM CA | 1.57 |
| 0.1% TRITON ® X-100, 250 mM Arginine, and 150 mM NaCl | 4.43 |
| 25 mM CA, 250 mM Arginine, and 150 mM NaCl | 2.04 |
| 100 mM Arginine, 150 mM Guanidine, 150 mM NaCl, and 25 mM CA | 1.21 |

Furthermore, viral clearance from selected wash solutions was assessed by using two model virus: xenotropic murine leukemia virus (X-MulV) and minute virus of mice (MVM) by spike-in study. The compositions and results are shown in Table 2. The results show that, compared with the control wash solution of 5 mM succinic acid at pH 5.8, there was a 1.7-log (arginine) or 0.8-log (arginine+guanidine) improvement in X-MulV clearance and a 1.3-log improvement in MVM clearance with either arginine- or arginine+guanidine-containing wash solutions.

TABLE 2

Spike-in Viral Clearance Study

| | Process Step | Log10 Reduction Value (LVR) | |
|---|---|---|---|
| | | X-MuLV | MVM |
| MabSelect SuRe Wash | 250 mM Arginine, 0.1% TRITON ® X-100, 150 mM NaCl, pH 7.5 | 5.86 | 3.08 |
| | | 4.78 | 3.03 |
| | 5 mM Succinic Acid, pH 5.8 control | 3.07 | 1.77 |
| | 100 Arginine + 150 Guanidine + 25 mM Sodium Caprylate + 150 mM NaCl, pH 7.5 | 3.84 | 3.05 |

Example 2—Wash Solutions for Cation Exchange Chromatography

Materials and Methods

A polymeric ion-exchange chromatography resin (Poros™ XS, Life Technologies Corp., Carlsbad, Calif.) and a resin composed of 6% agarose beads crosslinked with quaternary ammonium (Q) strong anion exchange groups (Q Sepharose® Fast Flow, GE-Healthcare Life Sciences, Marlborough, Mass.) were utilized for CEX chromatography. All buffer solutions used in this study were prepared using ultrapure water obtained from a water purification system (EMD Millipore, Billerica Mass.). Chemicals used for buffer and solution preparation were from JT Baker (Philipsburg, N.J.). All chromatographic experiments were carried out on Akta Avant chromatography system (GE Healthcare Life Sciences, Marlborough, Mass.).

The cation exchange chromatography column was equilibrated with a pH 5.5, low conductivity (<5 mS/cm) equilibration buffer for 5 CV (column volume). After equilibration, pH adjusted Protein A purified product pool (pH 5.5) was loaded onto the column at a load capacity of 50-80 grams of mAb per liter of resin. Following load application, the column was first washed with 3 CV of EQ buffer, followed by a Wash 2 with 5 CV of the candidate wash buffer. The column was subsequently washed with a Wash 3 buffer using 5 CV of 10 mM phosphate, pH 6.0 buffer. The mAb eluted from the column using 5 CV of 20 mM phosphate pH 7.0 buffer. The cleaning in place was applied after production.

Quantitative ELISA-Host Cell Protein (HCP)

Host Cell Protein (HCP) was determined by the CHO Host Cell Proteins 3rd Generation kit (Immunoenzymetric Assay for the Measurement of CHO Host Cell Proteins, Catalog #F550, Cygnus Technologies, Southport, N.C.) following manufacturer's protocol. The absorbance data at 450/650 nm were acquired on the SpectraMax Plus microplate reader and analyzed with SoftMaxPro 6.4.2 software (Molecular Devices, Sunnyvale, Calif.). HCP values were calculated from a 4 parameter logistic fit of the standard curves generated from the standards included in the CHO Host Cell Proteins 3rd Generation kit.

HPLC-SEC

The purity of the product samples was analyzed by HPLC-SEC method on a TSK gel G3000SW column (7.5 mm ID×30 cm, 10 µm average particle size, Tosoh Bioscience, Japan) using a Waters HPLC system (2695 separation module and 2996 Photodiode Array Detector). PBS pH 6.8 buffer was used as the mobile phase at a flow rate of 1 ml/min. The injection amount was 100-125 gig protein.

Results and Discussion

The protein of interest used in the study was an anti-TL1a-antibody comprising a heavy chain variable region with the amino acid sequence of SEQ ID NO:5 or SEQ ID NO: 6 and a light chain variable region with the amino acid sequence of SEQ ID NO:7. A total of 4 detergent-containing wash solutions were investigated in the study. The study was essentially repeated with an anti-CGRP antibody ($V_H$ of SEQ ID NO:1, $V_L$ of SEQ ID NO:2), and an anti-CD38 antibody ($V_H$ of SEQ ID NO:3, $V_L$ of SEQ ID NO:4). The Wash 2 buffer recipes and the results are shown in Tables 3 to 8.

TABLE 3

CEX Wash 2 Buffer Recipes for the Anti-TL1a-Antibody

| | Component | Quantity (g/l) |
|---|---|---|
| 10 mM Sodium Phosphate, 0.2% TRITON ® X-100 (w/v) pH 6.3 | Sodium Phosphate, Monobasic, monohydrate | 1.09 |
| | Sodium Phosphate, Dibasic heptahydrate | 0.57 |
| | TRITON ® X-100 | 2 |
| 10 mM Sodium Phosphate, 0.5% TRITON ® X-100 (w/v) pH 6.3 | Sodium Phosphate, Monobasic, monohydrate | 1.09 |
| | Sodium Phosphate, Dibasic heptahydrate | 0.57 |
| | TRITON ® X-100 | 5 |

TABLE 3-continued

CEX Wash 2 Buffer Recipes for the Anti-TL1a-Antibody

| | Component | Quantity (g/l) |
|---|---|---|
| 10 mM Sodium Phosphate, 0.3% PS 80 (w/v) pH 6.3 | Sodium Phosphate, Monobasic, monohydrate | 1.09 |
| | Sodium Phosphate, Dibasic heptahydrate | 0.57 |
| | Polysorbate 80 | 3 |
| 10 mM Sodium Phosphate, 0.6% PS 80 (w/v) pH 6.3 | Sodium Phosphate, Monobasic, monohydrate | 1.09 |
| | Sodium Phosphate, Dibasic heptahydrate | 0.57 |
| | Polysorbate 80 | 6 |

TABLE 4

Product Quality - Anti-TL1a Ab

| Wash Condition | Yield % | SEC-monomer % | HCP (ppm) | Residual Surfactant |
|---|---|---|---|---|
| Control | 99 | 99.2 | 12 | NT |
| 0.2% TRITON ®-X-100 | 96 | 99.2 | 7 | NT |
| 0.5% TRITON ®-X-100 | 99 | 98.8 | 5 | NT |
| 0.3% PS-80 | 100 | 99.1 | 6 | <LOQ |
| 0.6% PS-80 | 98 | 99.0 | 7 | <LOQ |

Control condition is no wash 1
NT: Not tested

TABLE 5

CEX Wash 2 Buffer Recipes for the Anti-CGRP-Antibody

| Buffers | Component | Quantity (g/l) |
|---|---|---|
| 25 mM Sodium Acetate, 10 mM NaCl, 0.2% TRITON ® X-100 (w/v) pH 6.3 | Glacial Acetic Acid | 0.17 |
| | Sodium Acetate Trihydrate | 3.02 |
| | Sodium Chloride | 7.89 |
| | TRITON ® X-100 | 2 |
| 25 mM Sodium Acetate, 10 mM, NaCl 0.5% TRITON ® X-100 (w/v) pH 6.3 | Glacial Acetic Acid | 0.17 |
| | Sodium Acetate Trihydrate | 3.02 |
| | Sodium Chloride | 7.89 |
| | TRITON ® X-100 | 5 |
| 25 mM Sodium Acetate, 10 mM NaCl, 0.3% PS 80 (w/v) pH 6.3 | Glacial Acetic Acid | 0.17 |
| | Sodium Acetate Trihydrate | 3.02 |
| | Sodium Chloride | 7.89 |
| | Polysorbate 80 | 3 |
| 25 mM Sodium Acetate, 10 mM NaCl, 0.6% PS 80 (w/v) pH 6.3 | Glacial Acetic Acid | 0.17 |
| | Sodium Acetate Trihydrate | 3.02 |
| | Sodium Chloride | 7.89 |
| | Polysorbate 80 | 6 |

TABLE 6

Product Quality

| Wash Condition | Yield % | SEC-monomer % | HCP (ppm) | Residual Surfactant |
|---|---|---|---|---|
| Control (no wash1) | 96 | 98.3 | 78 | NT |
| 0.2% TRITON ® X-100 | 96 | 98.4 | 70 | NT |
| 0.5% TRITON ® X-100 | >99 | 98.2 | 71 | NT |
| 0.3% PS 80 | >99 | 98.3 | 86 | <LOQ |
| 0.6% PS 80 | >99 | 98.3 | 81 | <LOQ |

NT: Not tested

TABLE 7

Wash 2 Buffer Recipes for the Anti-CD38-Antibody

| | Component | Quantity (g/l) |
|---|---|---|
| 50 mM Na-Acetate, 25 mM Arginine, 5 mM Histidine, 11 mM Nacl, 0.3% (w/v) PS-80, pH 5.5 | Sodium Acetate Trihydrate | 5.44 |
| | Glacial Acetic Acid | 0.6 |
| | L-Arginine HCl | 5.26 |
| | L-Histidine | 0.775 |
| | Sodium Chloride | 0.65 |
| | Polysorbate 80 | 3 |
| 50 mM Na-Acetate, 25 mM Arginine, 5 mM Histidine, 11 mM Nacl, 0.6% (w/v) PS80, pH 5.5 | Sodium Acetate Trihydrate | 5.44 |
| | Glacial Acetic Acid | 0.6 |
| | L-Arginine HCl | 5.26 |
| | L-Histidine | 0.775 |
| | Sodium Chloride | 0.65 |
| | Polysorbate 80 | 6 |
| 50 mM Na-Acetate, 25 mM Arginine, 5 mM Histidine, 11 mM Nacl, 0.2% (w/v) TRITON ® X-100, pH 5.5 | Sodium Acetate Trihydrate | 5.44 |
| | Glacial Acetic Acid | 0.6 |
| | L-Arginine HCl | 5.26 |
| | L-Histidine | 0.775 |
| | Sodium Chloride | 0.65 |
| | TRITON ® X-100 | 2 |
| 50 mM Na-Acetate, 25 mM Arginine, 5 mM Histidine, 11 mM Nacl, 0.5% (w/v) TRITON ® X-100, pH 5.5 | Sodium Acetate Trihydrate | 5.44 |
| | Glacial Acetic Acid | 0.6 |
| | L-Arginine HCl | 5.26 |
| | L-Histidine | 0.775 |
| | Sodium Chloride | 0.65 |
| | TRITON ® X-100 | 5 |

TABLE 8

Product Quality

| Wash Condition | Yield % | SEC-monomer % | HCP (ppm) | Residual Surfactant |
|---|---|---|---|---|
| Control (no wash 1) | 95 | 99.0 | 110 | NT |
| 0.2% TX-100 | 97 | 99.1 | 106 | NT |
| 0.5% TX-100 | 98 | 99.2 | 120 | NT |
| 0.3% PS 80 | 94 | 98.9 | 125 | <LOQ |
| 0.6% PS 80 | 92 | 99.0 | 123 | <LOQ |

NT: Not tested

Compared with control conditions without surfactants, all four surfactant-containing washes achieved similar impurity clearance for anti-TL1a, anti-CGRP and anti-CD38 antibody molecules. No residual surfactant in the elution pool was observed. The surfactant washes can be used to improve viral clearance while maintaining purified mAb quality.

TABLE 9

Viral Clearance Study Plan

| Solutions | MVM | X-MulV | Molecules |
|---|---|---|---|
| 25 mM Sodium Acetate, 10 mM NaCl, pH 5.5, control | X | X | anti-CGRP |
| 25 mM Sodium Acetate, 10 mM NaCl, 0.2% w/v TRITON ® X-100 pH 5.5 | | X | |
| 25 mM Sodium Acetate, 10 mM NaCl, 0.5% w/v TRITON ® X-100 pH 5.5 | X | X | |
| 25 mM Sodium Acetate, 10 mM NaCl, 0.3% w/v PS 80 pH 5.5 | | X | |
| 25 mM Sodium Acetate, 10 mM NaCl, 0.6% w/v PS 80 pH 5.5 | X | X | |
| 10 mM Sodium Phosphate, pH 6.3 | X | X | Anti-TL1A |
| 10 mM Sodium Phosphate, 0.2% TRITON ® X-100 (w/v) pH 6.3 | | X | |
| 10 mM Sodium Phosphate, 0.5% TRITON ® X-100 (w/v) pH 6.3 | X | X | |
| 10 mM Sodium Phosphate, 0.3% PS 80 (w/v) pH 6.3 | | X | |
| 10 mM Sodium Phosphate, 0.6% PS 80 (w/v) pH 6.3 | X | X | |

MVM: Infectivity assay
X-Mulv: Infectivity assay and qPCR assay

This study demonstrated that surfactant washes do not reduce product quality. Both residual surfactant and host cell proteins (HCP) can be cleared from product using surfactant washes.

Example 3—Cation Exchange as a Polishing Column and Capture Column, for Viral Clearance Materials and Methods
Cation Exchange Chromatography The chromatography column was first equilibrated, and then the load material was loaded on the column at a loading capacity of 40-100 mg/ml resin. After washing the column, monoclonal antibody (mAb) product was eluted from the column using an elution buffer. The cleaning in place (CIP) and sanitization in place (SIP) procedure was applied after product elution.

HPLC-Protein A Titer

Antibody titers were quantified on the Waters Alliance HPLC system using a 2.1 mm×30 mm analytical affinity column (Poros A affinity column, ABI. P/N: 2-1001-00) and appropriate standards. The quantity of standards ranged from 1 to 100 μg in an injection volume of 10 μL. Standards and samples were injected at 10 μL. The mobile phase A was 1×PBS buffer (ThermoFisher Scientific, Cat. #: 10010072). The mobile phase B was 12 mM HCl. The flow rate was 2.5 mg/mL. Antibodies were eluted out of the column at a gradient of 0-70% mobile phase B in 2.5 minutes. The elution peaks were integrated. The areas of the elution peaks were plotted against a linear standard curve derived from the areas and quantities of the standards to determine the antibody titer.

Solo VPE Protein Concentration Measurement

Protein concentrations were measured on the Solo VPE system (C Technologies Inc.). Typically 50-200 μL of samples were added into the small silica vessels for A 280 values. The protein concentrations were calculated by the Solo VPE system based on molecule extinction efficient.

HPLC-Size Exclusion Chromatography (SEC)

Antibody purity monomer percent (%) was analyzed by size exclusion chromatography on the Waters Alliance HPLC system using a 7.8 mm×30 cm size exclusion column (TSKgel G3000SW×1, P/N: 08541) preceded by a 6.0 mm×4.0 cm guard column (TOSOH TSKgel Guard SW×1, P/N: 08543). Typically samples were injected at 5.0 mg/mL in 30 μL. The isocratic mobile phase was 100 mM sodium phosphate, 250 mM sodium chloride pH 6.5. The flow rate was 0.5 mg/mL. High molecular weight species, dimers, monomers, and small molecular weight species were separated in 35 min. The percentage of each species was determined by the area of the peak divided by the total area of all the peaks.

Quantitative ELISA-Host Cell Production (HCP)

The HCP levels in samples were determined by ELISA assay using the Cygnus CHO HCP ELISA kit (Cygnus technologies, Cat. #: F550) following the manufacturer's protocol.

X-MuL V Spike-In Study

The CEX condition described above in this Example was performed using X-Mulv virus-spiked load material. The viral content in load and elution samples was analyzed by cell based infectivity assay, TCID 50. The LRV of each run was calculated by subtracting the log 10 total PFU of the elution sample from the log 10 total PFU of the load sample.

RVLP qPCR Assay

RVLPs (Retrovirus-like particles) were quantified by qPCR. The total nucleic acids were isolated from samples using the MagMAX™ Viral RNA Isolation Kit (ThermoFisher, Cat #AM1939) following the manufacture's protocol. The total nucleic acids were first treated with esDNase (to removal genomic DNA), then reverse transcribed to cDNA using the SuperScript™ IV VILO™ Master Mix with ezDNase™ Enzyme kit (ThermoFisher, Cat #AM1939). The cDNA samples were subjected to Taqman-based qPCR targeting the 3027 to 3125 bp region of the RVLP gene (GeneBank accession #: U09104.1). The primers used in the qPCR were CCTGAGTCACCGGACTGCAT (SEQ ID NO: 8) and ACCAGTCGCGAGCTGGAG (SEQ ID NO: 9). They were purchased from Integrated DNA Technologies (Skokie, Ill.). The Probe used in the qPCR was 5-FAM-AGGGAGCTACAGGCGG-MGBNFQ-3 (SEQ ID NO: 10), purchased from ThermoFisher. The standard for the qPCR was a double-stranded DNA fragment the covering the amplicon region. The qPCR assays were performed on the 7500FAST system (ThermoFisher) using the Taqman Fast Universal PCR master mix (ThermoFisher, Cat #4352046).

Residual Triton-100

Residual Triton X-100 concentrations were quantified by HPLC on the Waters Alliance HPLC system using a 4.6 mm×150 mm XDB-C18 column (Agilent Technologies, P/N: 993967-902). Samples were mixed with equal volume of 100% methanol and centrifuged at 4° C., 25,000× g for 30 minutes. The supernatant of the samples were saved for HPLC injection. Triton X-100 standards were diluted into 50% methanol prior to HPLC injection. A gradient of 78% to 100% methanol was employed to elute Triton X-100. The Triton X-100 peaks were integrated. Concentrations of Triton X-100 in samples were calculated by plotting the corresponding peak areas against those of the standards.

CEX as a Polishing Column

In order to evaluate the efficacy of CEX as a polishing column, two assays were conducted using different antibodies, resins, equilibration buffers, and wash conditions in the presence or absence of surfactants.

In the first assay, the process conditions listed in Table 10 were applied on an SP Sepharose Fast Flow (SPFF) resin to purify an anti-CGRP IgG2 antibody. The resin is a sepharose-based sulphopropyl strong cation exchange chromatography produced by GE. Similar resins include Fractogel EMD SO3-, and Capto S.

TABLE 10

Assay 1 - Process Conditions

| Process Step | Buffer | CV |
|---|---|---|
| EQ | 25 mM Sodium Acetate, 10 mM NaCl, pH 5.5 | ≥5 |
| Load | Protein A Purified mAb load at 50 g/L$_{resin}$ | |
| Wash 1 | 25 mM Sodium Acetate, 10 mM NaCl, pH 5.5 | ≥2 |
| Wash 2 | Variable to study | ≥5 |
| Wash 3 | 25 mM Sodium Acetate, 10 mM NaCl, pH 5.5 | ≥5 |
| Elution | 25 mM Sodium Acetate, 135 mM NaCl, pH 5.5 | 5 |

A viral spike-in study was conducted in which viral spiked load material was used. The wash 2 conditions tested and the results are shown in Table 11.

TABLE 11

Assay 1 - Viral Spike-in Study

| Wash 2 Condition | Yield % | LRV of X-MuLV |
|---|---|---|
| 25 mM Sodium Acetate, 10 mM NaCl, pH 5.5 | 96 | 3.7 |
| 25 mM Sodium Acetate, 10 mM NaCl, 0.5% Triton-100, pH 5.5 | >99 | >7.05[a] |

[a]Virus has been cleared to below detection.

These results demonstrate that the addition of 0.5% Triton in wash 2 significantly improves to log clearance of X-MuLV.

The product quality was also assessed using protein A-purified mAb as the load under the conditions summarized in Table 12, and the results are also reported in this table.

TABLE 12

Assay 1 - Product Quality

| Wash Condition | Yield % | SEC-monomer % | HCP (ppm) | Residual Surfactant % |
|---|---|---|---|---|
| Wash 2 and 3: 25 mM Sodium Acetate, 10 mM NaCl, pH 5.5 | 96 | 98.3 | 78 | NA |
| Wash 2: 25 mM Sodium Acetate, 10 mM NaCl, 0.5% Triton-100, pH 5.5 Wash 3: 25 mM Sodium Acetate, 10 mM NaCl, pH 5.5 | >99 | 98.2 | 71 | <DL |
| Wash 2: 25 mM Sodium Acetate, 10 mM NaCl, 0.5% Triton-100, pH 5.5 No Wash 3 | 91 | 97.6 | 91 | 0.008 |

DL = 0.002%

The results in Table 12 demonstrate that the addition of 0.5% Triton in wash 2 does not decrease product quality in terms of either monomer % or residual host cell protein (HCP). These results also demonstrate that wash 3 is able to remove residual surfactant to undetectable levels.

In the second assay, the process conditions listed in Table 13 were applied on an Poros XS resin (Thermo Scientific) to purify an anti-TL1a IgG1 antibody. This resin has cross-linked poly (styrenedivinylbenzene) polymer matrix with Sulfopropyl ligand.

TABLE 13

Assay 2 - Process Conditions

| Process Step | Buffer | CV |
|---|---|---|
| EQ | 25 mM Glycine, 10 mM Succinic Acid, pH 5.5 | ≥5 |
| Load | Protein A purified mAb, load at 85 g/L$_{resin}$ | |
| Wash 1 | 25 mM Glycine, 10 mM Succinic Acid, pH 5.5 | ≥2 |
| Wash 2 | Variable to study | ≥5 |
| Wash 3 | 10 mM Sodium Phosphate, pH 6.3 | ≥5 |
| Elution | 24 mM Sodium Phosphate, pH 6.9 | 8 |

A viral spike-in study was conducted in which viral spiked load material was used. The wash 2 conditions tested and the results are shown in Table 14.

TABLE 14

Assay 2 - Viral Spike-in Study

| Wash 2 Condition | Yield % | LRV of X-MuLV | LRV of X-Mulv qPCR |
|---|---|---|---|
| 10 mM Sodium Phosphate, pH 6.3 | >99 | 2.9 | 2.22 |
| 10 mM Sodium Phosphate, 0.5% Triton-100, pH 6.3 | >99 | 6.05 | 3.83 |
| 10 mM Sodium Phosphate, 0.5% Triton-100, pH 6.3 Pause 30 minutes at the end of the wash 2 | >99 | 6.25 | 4.01 |

These results demonstrate that, as in Assay 1, the addition of 0.5% Triton in wash 2 significantly improves to log clearance of X-MuLV in Assay 2. In addition, more than 6 log viral clearances could be achieved in 5 column volumes (CV) of wash, with or without a 30 minute pause at the end of wash 2.

The product quality was also assessed using protein A-purified mAb as the load under the conditions summarized in Table 15, and the results are also reported in this table.

TABLE 15

Assay 2 - Product Quality

| Wash Condition | Yield % | SEC-monomer % | HCP (ppm) | Residual Surfactant % |
|---|---|---|---|---|
| Wash 2 and 3: 25 mM Sodium Acetate, 10 mM NaCl, pH 5.5 | 96 | 98.3 | 78 | NA |
| Wash 2: 25 mM Sodium Acetate, 10 mM NaCl, 0.5% Triton-100, pH 5.5 Wash 3: 25 mM Sodium Acetate, 10 mM NaCl, pH 5.5 | >99 | 98.2 | 71 | <DL |
| Wash 2: 25 mM Sodium Acetate, 10 mM NaCl, 0.5% Triton-100, pH 5.5 No Wash 3 | 91 | 97.6 | 91 | 0.008 |

DL = 0.002%

The results in Table 15 demonstrate that, as in Assay 1, the addition of 0.5% Triton in wash 2 does not decrease product quality in terms of either monomer % or residual host cell protein (HCP) in Assay 2. However, residual surfactant was not as effectively removed without wash 3, possibly because Poros XS is a hydrophobic resin. In any case, addition of wash 3 reduced surfactant level to below the limit of detection.

CEX as a Capture Column

In order to evaluate the efficacy of surfactants' effect on CEX as a capture column, two assays were conducted using different resins, equilibration buffers, and wash conditions in the presence or absence of surfactants.

In the first assay, the process conditions listed in Table 16 were applied on an SPFF resin.

TABLE 16

Assay 1 - Process Conditions

| Process Step | Buffer | CV |
|---|---|---|
| EQ | 25 mM Sodium Acetate, 45 mM NaCl, pH 5.5 | ≥5 |
| Load | HCCF adjusted to pH 5.0, conductivity 7 mS/cm, load at 40 g/Lresin | |
| Wash 1 | 25 mM Sodium Acetate, 45 mM NaCl, pH 5.5 | ≥2 |
| Wash 2 | Variable to Study | Variable to study |
| Wash 3 | 25 mM Sodium Acetate, 10 mM NaCl, pH 5.5 | ≥5 |
| Elution | 25 mM Sodium Acetate, 250 mM NaCl, pH 5.5 | 5 |

Retroviral-like particle (RVLP) clearance was assessed using HCCF as the load material and the conditions listed in Table 17.

TABLE 17

Assay 1 - RVLP Clearance

| Wash Condition | Yield % | SEC-monomer % | HCP (ppm) | LRV of RVLP |
|---|---|---|---|---|
| Wash 2: 5 CV of 25 mM Sodium Acetate, 10 mM NaCl, pH 5.5 Wash 3: 5 CV of 25 mM Sodium Acetate, 10 mM NaCl, pH 5.5 | 96 | 97.0 | 40,744 | 1.6 |
| Wash 2: 5 CV of 25 mM Sodium Acetate, 10 mM NaCl, 0.5% Triton-100, pH 5.5 Wash 3: 5 CV of 25 mM Sodium Acetate, 10 mM NaCl, pH 5.5 | 97 | 98.7 | 18,873 | >3.7[a] |
| Wash 2: 1 CV of 25 mM Sodium Acetate, 10 mM NaCl, 0.5% Triton-100, pH 5.5 Wash 3: 5 CV of 25 mM Sodium Acetate, 10 mM NaCl, pH 5.5 | 96 | 98.7 | 23,490 | >3.7[a] |
| Wash 2: 1 CV of 25 mM Sodium Acetate, 10 mM NaCl, 0.5% Triton-100, pH 5.5 No Wash 3 | 97 | 95.6 | 27,086 | >3.7[a] |

[a]RVLP has been cleared to below detection.

These results demonstrate that the addition of 0.5% Triton in wash 2 improves RVLP clearance by 2 logs and also significantly increased HCP clearance. The volume of wash 2 did not impact viral clearance efficacy, and 1 column volume (CV) was sufficient for wash 2. However, increasing the volume of wash 2 did improve HCP clearance. Including wash 3 also improved HCP clearance.

Additional tests were conducted varying the wash 2 conditions as summarized in Table 18. In these tests, five column volumes (CVs) of wash 2 and five CVs of was 3 were applied. The results are also reported in Table 17.

TABLE 18

Assay 1 - Wash 2 Condition Study (Atoll column results)

| Wash 2 Conditions | Yield % | SEC-monomer % | HCP (ppm) | LRV of RVLP |
|---|---|---|---|---|
| 25 mM Sodium Acetate, 10 mM NaCl, pH 5.5 | 74 | 98.4 | 40,445 | 1.03 |
| 25 mM Sodium Acetate, 10 mM NaCl, 0.05% Triton, pH 5.5 | 87 | 98.4 | 34,844 | 2.39 |
| 25 mM Sodium Acetate, 10 mM NaCl, 0.1% Triton-100, pH 5.5 | 82 | 98.5 | 40,251 | >2.46[a] |
| 25 mM Sodium Acetate, 10 mM NaCl, 0.5% PS 20, pH 5.5 | 74 | 98.6 | 38,847 | 1.18 |
| 25 mM Sodium Acetate, 10 mM NaCl, 0.2% PS 20, pH 5.5 | 81 | 98.4 | 38,040 | 1.33 |
| 25 mM Sodium Acetate, 10 mM NaCl, 0.5% PS 80, pH 5.5 | 81 | 98.4 | 44,535 | 1.27 |
| 25 mM Sodium Acetate, 10 mM NaCl, 0.5% NP 40, pH 5.5 | 82 | 98.4 | 39,684 | >2.46[a] |
| 25 mM Sodium Acetate, 10 mM NaCl, 0.1% LDAO, pH 5.5 | 81 | 97.2 | 9,132 | >2.09[a] |
| 25 mM Sodium Acetate, 10 mM NaCl, 0.05% LDAO, pH 5.5 | 88 | 97.5 | 21,749 | >2.09[a] |
| 25 mM Sodium Acetate 10 mM NaCl, 0.2% SB-12, pH 5.5 | 89 | 99.8 | 28,223 | >3.53[a] |
| 25 mM Sodium Acetate 10 mM NaCl, 1.0% SB-12, pH 5.5 | 86 | 97.1 | 19,509 | >3.53[a] |
| 25 mM, Sodium Acetate 10 mM NaCl, 0.2% SB-14, pH 5.5 | 92 | 98.7 | 25,600 | >3.53[a] |
| 25 mM Sodium Acetate 10 mM NaCl, 0.5% SB-14, pH 5.5 | 93 | 97.6 | 19,819 | >3.53[a] |

LDAO = Lauryldimethylamine N-oxide;
SB-12 = Sulfobetaine-12; and
SB-14 = Sulfobetaine-14
[a]RVLP has been cleared to below detection.

The results in Table 18 demonstrate that the addition of 0.05% Triton, >0.2% of SB-12, >0.2% of SB-14, >0.5% of NP-40 and >0.05% LDAO were all effective for RVLP clearance. They were able to clear RVLP to below detection. LDAO, SB-12, and SB-14 are also able to significantly improve HCP clearance.

In the second assay, the process conditions listed in Table 19 were applied on an Poros XS resin.

TABLE 19

Assay 2 - Process Conditions

| Process Step | Buffer | CV |
|---|---|---|
| EQ | 25 mM Glycine, 60 mM Succinic Acid, pH 5.5 | ≥5 |
| Load | HCCF adjusted to pH 5.5, conductivity 7 mS/cm, load at 40 g/L$_{resin}$ | |
| Wash 1 | 25 mM Glycine, 60 mM Succinic Acid, pH 5.5 | ≥2 |
| Wash 2 | Variable to study | Variable to study |
| Wash 3 | 10 mM Sodium Phosphate, pH 6.3 | ≥5 |
| Elution | 24 mM Sodium Phosphate, pH 6.9 | 8 |

Retroviral-like particle (RVLP) clearance was assessed using HCCF as the load material and the conditions listed in Table 20. The results are also shown in this table.

TABLE 20

Assay 2 - RVLP Clearance

| Wash Condition | Yield % | SEC-monomer % | HCP (ppm) | LRV of RVLP |
|---|---|---|---|---|
| Wash 2: 1 CV of 10 mM Sodium Phosphate, 0.5% Triton-100, pH 6.3 Wash 3: 5 CV of 10 mM Sodium Phosphate, pH 6.3 | 96 | 99.0 | 8,325 | 4.3 |
| Wash 2: 1 CV of 10 mM Sodium Phosphate, 0.5% Triton-100, pH 6.3 No Wash 3 | 94 | 98.6 | 17,145 | 4.3 |

These results demonstrate that HCP is significantly lower with wash 3 than without.

Additional tests were conducted varying the wash 2 conditions as summarized in Table 21. In these tests, five column volumes (CVs) of wash 2 and five CVs of was 3 were applied. The results are also reported in Table 21.

TABLE 21

Assay 2 - Wash 2 Condition Study (Atoll column results)

| Wash 2 Conditions | Yield % | SEC-monomer % | HCP (ppm) | LRV of RVLP |
|---|---|---|---|---|
| 10 mM Sodium Phosphate, 0.05% Triton, pH 6.3 | 77 | 99.0 | 11,398 | 2.34 |
| 10 mM Sodium Phosphate, 0.1% Triton-100, pH 6.3 | 67 | 98.9 | 12,356 | 3.10 |
| 10 mM Sodium Phosphate, 0.5% Triton-100, pH 6.3 | 73 | 99.0 | 11,352 | >3.82[a] |
| 10 mM Sodium Phosphate, 0.5% PS 20, pH 6.3 | 71 | 98.9 | 10,423 | 2.78 |
| 10 mM Sodium Phosphate, 0.2% PS 20, pH 6.3 | 73 | 99.0 | 44,481 | 2.73 |
| 10 mM Sodium Phosphate, 0.5% PS 80, pH 6.3 | 72 | 98.9 | 12,207 | 2.58 |
| 10 mM Sodium Phosphate, 0.5% NP 40, pH 6.3 | 75 | 98.9 | 10,026 | 2.65 |
| 10 mM Sodium Phosphate, 10 mM NaCl, pH 6.3 | 72 | 99.0 | 9,877 | 2.09 |

[a]RVLP has been cleared to below detection.

The results in Table 21 demonstrate that concentrations of at least 0.1% Triton are effective in viral clearance.

In sum, the results described here in Example 3 demonstrate that the addition of a surfactant to a CEX wash (wash 2) improves clearance of retrovirus, whether the CEX is being used in a polishing step or a capturing step. The addition of the surfactant does not adversely affect process yield or product quality in terms of either HCP or monomer purity (%). This surfactant-based virus removal can be achieved on sepharose matrix resins and synthetic polymer matrix resins, and one column volume is sufficient to achieve effective RVLP clearance. Furthermore, wash 3 improves HCP clearance, and LDAO and 0.5% Triton each improve HCP clearance on sepharose-based resins.

The invention is not limited to the embodiments described and exemplified above, but is capable of variation and modification within the scope of the appended claims.

Various publications, including patents, patent applications, accession numbers, technical articles and scholarly articles are cited throughout the specification. Each of these cited publications is incorporated by reference herein, in its entirety and for all purposes.

```
                    Sequence Listing

Anti-CGRP VH (SEQ ID NO: 1)
    1     EVQLVESGGG LVQPGGSLRL SCAASGFTFS NYWISWVRQA PGKGLEWVAE    50

51     IRSESDASAT HYAEAVKGRF TISRDNAKNS LYLQMNSLRA EDTAVYYCLA   100

101     YFDYGLAIQN YWGQGTLVTV SS

Anti-CGRP VL (SEQ ID NO: 2)
    1     EIVLTQSPAT LSLSPGERAT LSCKASKRVT TYVSWYQQKP GQAPRLLIYG    50

51     ASNRYLGIPA RFSGSGSGTD FTLTISSLEP EDFAVYYCSQ SYNYPYTFGQ   100

101     GTKLEIK
```

Sequence Listing

```
Anti-CD38 VH (SEQ ID NO: 3)
    1    EVQLVQSGAE VKKPGATVKI SCKVSGYTFT DSVMNWVQQA PGKGLEWMGW    50

51    IDPEYGRTDV AEKFQGRVTI TADTSTDTAY MELSSLRSED TAVYYCARTK   100

101    YNSGYGFPYW GQGTTVTVSS

Anti-CD38 VL (SEQ ID NO: 4)
    1    DIQMTQSPSS LSASVGDRVT ITCKASQNVD SDVDWYQQKP GKAPKLLIYK    50

51    ASNDYTGVPS RFSGSGSGTD FTFTISSLQP EDIATYYCMQ SNTHPRTFGG   100

101    GTKVEIKR

Anti-TL 1a VH1 (SEQ ID NO: 5)
QVQLVQSGAEVKKPGASVKVSCKASGYTFTSYDINWVRQAPGQGLEWMGWLNPNSGNTGY
AQKFQGRVTMTADRSTSTAYMELSSLRSEDTAVYYCAREVPETAAFEYWGQGTLVTVSS Anti-TL 1a VH2 (SEQ ID NO: 6)
QVQLVQSGAEVKKPGASVKVSCKASGYTFTSYDINWVRQAPGQGLEWMGWLNPNSGYTGY
AQKFQGRVTMTADRSTSTAYMELSSLRSEDTAVYYCAREVPETAAFEYWGQGTLVTVSS Anti-TL 1a VL (SEQ ID NO: 7)
QSVLTQPPSVSGAPGQRVTISCTSSSSDIGAXXGVXWYQQLPGTAPKLLIEGYYNRPSGVPDRF
SGSKSGTSASLTITGLLPEDEGDYYCQSXDGTLSALFGGGTKLTVLG
Xaa 32 is G or A
Xaa 33 is L or S or Q
Xaa 36 is H or L
Xaa 93 is Y or F or W
```

We claim:

1. A method of purifying a protein of interest bound to a cation exchange (CEX) chromatography support comprising applying a wash solution comprising ≥0.2% Sulfobetaine-12 (SB-12) to the CEX chromatography support, wherein the wash solution clears retroviral like particles (RVLP) to below detection levels as measured by a log reduction value (LRV) and clears host cell proteins (HCP).

2. The method of claim 1, further comprising loading a mixture comprising a protein of interest and one or more contaminant proteins, aggregates, and/or viruses onto the CEX chromatography support before applying the wash solution comprising SB-12 to the CEX chromatography support, and then eluting the protein of interest from the CEX chromatography support after applying the wash solution comprising SB-12 to the CEX chromatography support, thereby forming a purified eluate of the protein of interest.

3. A method for purifying a protein of interest, comprising loading a mixture comprising a protein of interest and one or more contaminant proteins, aggregates, and/or viruses onto a CEX chromatography support, washing the CEX chromatography support with an aqueous wash solution comprising ≥0.2% Sulfobetaine-12 (SB-12) to elute the one or more contaminant proteins, aggregates, and/or viruses from the CEX chromatography support, and then eluting the protein of interest from the CEX chromatography support, thereby forming a purified eluate of the protein of interest, wherein the wash solution clears retroviral like particles (RVLP) to below detection levels as measured by a log reduction value (LRV) and clears host cell proteins (HCP).

4. The method of claim 2, wherein the CEX chromatography support is a sepharose matrix resin.

5. The method of claim 2, wherein the CEX chromatography support is a synthetic polymer matrix resin or wherein the CEX chromatography support is not a hydrophobic resin.

6. The method of claim 2, further comprising applying a subsequent wash solution to the CEX chromatography support before eluting the protein of interest from the CEX chromatography support.

7. The method of claim 2, wherein the mixture comprising a protein of interest and one or more contaminant proteins, aggregates, and/or viruses is a harvest cell culture fluid (HCCF).

8. The method of claim 2, wherein the method does not comprise protein A purification.

9. The method of claim 2, wherein the mixture comprising a protein of interest and one or more contaminant proteins, aggregates, and/or viruses is an eluate of a chromatography step.

10. The method of claim 1, comprising:
a) loading a mixture comprising a protein of interest and one or more contaminants, aggregates and/or viruses onto a protein A chromatography support,
b) washing the protein A chromatography support with a protein A chromatography wash solution comprising one or more surfactants to remove the one or more contaminant proteins, aggregates and/or viruses from the protein A chromatography support,
c) eluting the protein of interest from the protein A chromatography support, and
d) loading the eluate comprising the protein of interest onto the cation exchange (CEX) chromatography support before applying the wash solution comprising SB-12 to the CEX chromatography support; wherein the wash solution removes the one or more contaminant proteins, aggregates and/or viruses from the CEX chromatography support, and then eluting the protein of interest from the CEX chromatography support after applying the wash solution comprising SB-12 to the CEX chromatography support, thereby forming a purified eluate of the protein of interest.

11. The method of claim 2, wherein the contaminant proteins are host cell proteins.

12. The method of claim 1, wherein the LRV is achieved by applying 1 column volume (CV), 2 CVs, 3 CVs, 4 CVs, or 5 CVs of the wash.

13. The method of claim 2, further comprising applying a wash solution that does not comprise a surfactant to the CEX chromatography support prior to applying the wash solution comprising SB-12 to the CEX chromatography support.

14. The method of claim 2, further comprising treating the purified eluate of the protein of interest with diafiltration, ultrafiltration, or both diafiltration and ultrafiltration.

15. The method of claim 2, further comprising loading the purified eluate of the protein of interest onto a membrane chromatography support and collecting flow through comprising a further-purified eluate from the membrane chromatography support.

16. The method of claim 2, wherein the method does not comprise an anion exchange chromatography step.

17. The method of claim 2, further comprising subjecting the eluate to a viral inactivation step or further comprising filtering the purified eluate of the protein of interest to remove viruses.

18. The method of claim 2, further comprising formulating the purified eluate of the protein of interest as a composition including a pharmaceutically acceptable excipient.

19. The method of claim 2, further comprising expressing the protein of interest and one or more contaminant proteins in a bioreactor having a capacity of at least 250 liters.

20. The method of claim 2, wherein the protein of interest comprises an antibody or antigen binding fragment thereof, or fusion protein construct thereof.

21. The method of claim 2, wherein the CEX chromatography wash solution further comprises arginine, histidine, sodium chloride, sodium phosphate, or sodium acetate.

22. The method of claim 2, wherein the CEX chromatography wash solution comprises a pH of about 5.0 to 7.0.

23. A preparation of a protein of interest produced by the method of claim 1.

24. A composition comprising a preparation of a protein of interest produced by the method of claim 1 and a pharmaceutically acceptable excipient.

25. A composition comprising a virus-inactivated preparation of a protein of interest and a pharmaceutically acceptable excipient, produced by the method of claim 1.

26. The method of claim 2, wherein the wash solution comprises 0.2% SB-12.

27. The method of claim 2, wherein the wash solution comprises 1% SB-12.

28. The method of claim 2, wherein the wash solution further comprises 25 mM sodium acetate and 10 mM NaCl and has a pH of 5.5.

* * * * *